United States Patent
Burnett et al.

(10) Patent No.: US 11,102,200 B1
(45) Date of Patent: Aug. 24, 2021

(54) SECURE AUTHENTICATION USING MULTIPLE AUTHENTICATION FACTORS IN A NON-SECURE DOMAIN

(71) Applicant: Architecture Technology Corporation, Minneapolis, MN (US)

(72) Inventors: Benjamin L. Burnett, Prior Lake, MN (US); Ranga Ramanujan, Medina, MN (US)

(73) Assignee: ARCHITECTURE TECHNOLOGY CORPORATION, Minneapolis, MN (US)

( * ) Notice: Subject to any disclaimer, the term of this patent is extended or adjusted under 35 U.S.C. 154(b) by 61 days.

(21) Appl. No.: 15/870,492

(22) Filed: Jan. 12, 2018

Related U.S. Application Data

(60) Provisional application No. 62/489,325, filed on Apr. 24, 2017.

(51) Int. Cl.
*H04L 29/06* (2006.01)
*G06K 9/00* (2006.01)

(52) U.S. Cl.
CPC ...... *H04L 63/0853* (2013.01); *G06K 9/00892* (2013.01); *H04L 63/083* (2013.01); *H04L 63/0861* (2013.01)

(58) Field of Classification Search
CPC . H04L 67/306; H04L 63/0853; H04L 63/083; H04L 63/0861; H04L 67/04; H04L 67/12; H04L 67/18; H04L 67/22; G06K 9/00892; G06F 21/316; G06F 21/32; G06F 2221/2111
See application file for complete search history.

(56) References Cited

U.S. PATENT DOCUMENTS

| | | | |
|---|---|---|---|
| 7,669,235 B2 * | 2/2010 | Hunt | H04L 9/3273 726/18 |
| 8,561,142 B1 * | 10/2013 | Sobel | G06F 21/6218 726/3 |
| 8,970,348 B1 | 3/2015 | Evans et al. | |
| 9,363,264 B2 * | 6/2016 | Novack | H04L 63/10 |
| 9,419,799 B1 | 8/2016 | Chung | |

(Continued)

OTHER PUBLICATIONS

"Multi-Factor Authentication," Wikipedia, the free encyclopedia, retrieved from https://en.wikipedia.org/wiki/Multi-factor_authentication, on Jan. 18, 2018, 8 pp.

(Continued)

*Primary Examiner* — Trang T Doan
(74) *Attorney, Agent, or Firm* — Shumaker & Sieffert, P.A.

(57) ABSTRACT

In general, the techniques of this disclosure describe a computing device that is configured to verify an identity of a user based on authentication factors received from multiple authentication devices. The computing device, which may be configured to operate as a server device, may receive an authentication factor from at least three authentication devices in a group of three or more authentication devices via a guard device. The computing device may determine a probability that the respective user of each respective authentication device is a particular trusted user based on the received authentication factors. If the probability exceeds a threshold authentication probability, the computing device may send an authentication confirmation to a client device.

20 Claims, 14 Drawing Sheets

(56) References Cited

U.S. PATENT DOCUMENTS

| | | | |
|---|---|---|---|
| 9,524,399 B1 | 12/2016 | Takahashi | |
| 9,858,441 B2* | 1/2018 | Brown | G06F 1/28 |
| 10,091,230 B1* | 10/2018 | Machani | G06F 21/316 |
| 10,164,974 B2* | 12/2018 | Spencer | G06Q 30/06 |
| 2002/0069369 A1 | 6/2002 | Tremain | |
| 2004/0003284 A1 | 1/2004 | Campbell et al. | |
| 2004/0044902 A1 | 3/2004 | Luthi | |
| 2005/0198412 A1 | 9/2005 | Pedersen et al. | |
| 2007/0192585 A1 | 8/2007 | Briancon et al. | |
| 2008/0289027 A1 | 11/2008 | Yariv et al. | |
| 2009/0064309 A1 | 3/2009 | Boodaei et al. | |
| 2009/0077375 A1 | 3/2009 | Anspach | |
| 2014/0119727 A1 | 5/2014 | Ousley et al. | |
| 2014/0157381 A1 | 6/2014 | Disraeli | |
| 2014/0304773 A1* | 10/2014 | Woods | H04L 63/08 726/3 |
| 2015/0161370 A1* | 6/2015 | North | G06F 21/32 726/5 |
| 2015/0281225 A1 | 10/2015 | Schoen et al. | |
| 2015/0363582 A1* | 12/2015 | Sheller | G06F 21/31 726/17 |
| 2016/0233946 A1* | 8/2016 | Wengrovitz | G05D 1/0011 |
| 2016/0241523 A1* | 8/2016 | Ahn | H04L 63/0428 |
| 2017/0193211 A1* | 7/2017 | Blake | H04L 67/12 |
| 2017/0242995 A1* | 8/2017 | Bassenye-Mukasa | G06F 16/24575 |
| 2018/0041475 A1 | 2/2018 | Rai | |
| 2018/0054312 A1 | 2/2018 | Kamal | |
| 2018/0095900 A1 | 4/2018 | Sarangdhar et al. | |

OTHER PUBLICATIONS

Joint Tactical Radio System, Wikipedia, the free encyclopedia, retrieved from https://en.wikipedia.org/wiki/Joint_Tactical_Radio_System, on Jan. 18, 2018, 9 pp.

"Equipping the Warfighter with Small Business Ingenuity," Phase III Desk Reference,V1.0, U.S. Air Force, 2016 (Applicant points out, in accordance with MPEP 609.04(a), that the year of publication, 2016, is sufficiently earlier than the effective U.S. filing date, 2018, so that the particular month of publication is not in issue.) p. 16.

"Technavio Says Global EEG and ECG Biometrics Market Will Reach $42.14 Million by 2020," Techanvio.com, Apr. 7, 2016, 2 pp.
Keller, "ATCorp to build SWaP-Optimized Airborne Networking Router Prototypes for Carrier-Based Aircraft," Military and Aerospace Electronics, Jan. 19, 2017, 4 pp.
Lugovaya, "Biometric Human Identification Based on ECG," physionet.org, 2005 (Applicant points out, in accordance with MPEP 609.04(a), that the year of publication, 2005, is sufficiently earlier than the effective U.S. filing date, 2018, so that the particular month of publication is not in issue.) 9 pp.
"A Heart to my Key," economist.com., https://www.economist.com/blogs/babbage/2013/05/biometrics, May 9, 2013, 4 pp.
"NYMI Band: Product Overview," Nymi, retrieved from https://nymi.com/product_overview, on Jan. 18, 2018, 2 pp.
U.S. Appl. No. 15/866,046, filed Jan. 9, 2018, by Charan et al.
U.S. Appl. No. 15/866,097, filed Jan. 9, 2018, by Bonney et al.
U.S. Appl. No. 62/489,320, by Ranga Ramanujan et al., filed May 3, 2017.
"Gartner Says Worldwide Information Security Spending will Grow 7 Percent to Reach $86.4 Billion in 2017," accessed from gartner.com, Aug. 16, 2017, 4 pp.
"Harris Still in Neutral Zone," Zacks Equity Research, Feb. 13, 2012, 2 pp.
"military Communications Market Worth USD 40.82 Billion by 2020," MarketWatch, Sep. 11, 2015, 2 pp.
"Military Tablet Wars: Windows Gaining on Apple," Kiosk Industry, Feb. 27, 2016, 1 pp.
De Renesse, "Virtual Digital Assistants to Overtake World Population by 2021," accessed from informa.com, May 17, 2017, 3 pp.
Office Action from U.S. Appl. No. 15/866,046, dated Jan. 2, 2020, 27 pp.
U.S. Appl. No. 15/959,709, filed Apr. 23, 2018, by Ramanujan et al.
Notice of Allowance from U.S. Appl. No. 15/866,097, dated Jul. 17, 2020,14pp.
Office Action from U.S. Appl. No. 15/866,097, dated Mar. 4, 2020, 20 pp.
Response to Office Action dated Mar. 23, 2020, from U.S. Appl. No. 15/866,046, filed Jan. 9, 2018, 10 pp.
Response to Office Action dated Mar. 4, 2020, from U.S. Appl. No. 15/866,097, filed Jun. 4, 2020, 15 pp.
Notice of Allowance from U.S. Appl. No. 15/866,046, dated Jun. 8, 2020, 8 pp.

* cited by examiner

SECURE AUTHENTICATION USING MULTIPLE AUTHENTICATION FACTORS IN A NON-SECURE DOMAIN

This application claims the benefit of U.S. Provisional Application No. 62/489,325, filed Apr. 24, 2017, the entire content of which is incorporated herein by reference.

STATEMENT REGARDING FEDERALLY SPONSORED RESEARCH OR DEVELOPMENT

This invention was made with Government support under Contract FA8750-17-C-0244 awarded by the United States Air Force. The Government may have certain rights in this invention.

TECHNICAL FIELD

The disclosure relates to handling and processing secured data.

BACKGROUND

Field-users of secure mobile devices may employ multiple digital assets in the field for digital communications and other applications. Examples may include voice applications and surveillance unmanned aerial vehicles (UAVs). Some data sources do not support any secured level classification. Some integrated systems may utilize commercial off-the-shelf (COTS) devices for secured level tactical and front-line use (e.g., common operating picture, data feeds, real-time communications, etc.). Even though the non-secured data sources may improve the effectiveness of field-users and improve the ability to complete missions, these systems may not be capable of connecting with secured devices because of the difference in security classification levels. For instance, rules governing the operation of secure devices preclude direct connection of such devices to non-secure devices or devices at a different classification level than the secured device. As such, the system may block the non-secured data from flowing into the secured domain and may control or block any/all data flowing into the non-secured domain.

SUMMARY

In general, the techniques of this disclosure describe a computing device that is configured to verify an identity of a user based on authentication factors received from multiple authentication devices. The computing device, which may be configured to operate as a server device, may receive an authentication factor from at least three authentication devices in a group of three or more authentication devices via a guard device (e.g., a cross-domain solution or CDS). A guard device may be any standalone device, hardware component of a larger system, or software component of a device that receives information from a device that is in a non-secure domain, analyzes the information to ensure its integrity, and forwards the information to a device in a secure domain. The guard device may also receive information from a device in a secure domain and forward the information to another device in the secure domain. The computing device may determine a probability that the respective user of each respective authentication device is a particular trusted user based on the received authentication factors. If the probability exceeds a threshold authentication probability, the computing device may send an authentication confirmation to a client device.

In one example, the disclosure is directed to a method including receiving, by a server device in a secure domain, via a guard device, an authentication factor from at least three authentication devices in a group of three or more authentication devices. At least one authentication device in the group of three or more authentication devices is in a non-secure domain, and each respective authentication factor comprises a respective identifier of a respective user of the respective authentication device. The method further includes determining, by the server device, a probability that the respective user of each respective authentication device is a particular trusted user based on the received authentication factors. The method also includes comparing, by the server device, the probability to a threshold authentication probability. The method further includes, responsive to determining that the probability exceeding the threshold authentication probability, sending, by the server device to a client device, an authentication confirmation comprising an indication of the particular trusted user.

In another example, the disclosure is directed to a server device comprising one or more communication units and one or more processors. The one or more processors are configured to receive, via a guard device, an authentication factor from at least three authentication devices in a group of three or more authentication devices. The server device is located in a secure domain. At least one authentication device in the group of three or more authentication devices is in a non-secure domain, and each respective authentication factor comprises a respective identifier of a respective user of the respective authentication device. The one or more processors are further configured to determine a probability that the respective user of each respective authentication device is a particular trusted user based on the received authentication factors. The one or more processors are also configured to compare the probability to a threshold authentication probability. The one or more processors are further configured to, responsive to determining that the probability exceeding the threshold authentication probability, send, to a client device, an authentication confirmation comprising an indication of the particular trusted user.

In another example, the disclosure is directed to a non-transitory computer readable storage medium storing instructions that, when executed by one or more processors of a server device cause the one or more processors to receive, via a guard device, an authentication factor from at least three authentication devices in a group of three or more authentication devices. The server device is located in a secure domain. At least one authentication device in the group of three or more authentication devices is in a non-secure domain, and each respective authentication factor comprises a respective identifier of a respective user of the respective authentication device. The instructions further cause the one or more processors to determine a probability that the respective user of each respective authentication device is a particular trusted user based on the received authentication factors. The instructions also cause the one or more processors to compare the probability to a threshold authentication probability. The instructions further cause the one or more processors to, responsive to determining that the probability exceeding the threshold authentication probability, send, to a client device, an authentication confirmation comprising an indication of the particular trusted user.

In another example, the disclosure is directed to a system including means for receiving, in a secure domain, via a guard device, an authentication factor from at least three authentication devices in a group of three or more authentication devices. At least one authentication device in the group of three or more authentication devices is in a non-secure domain, and each respective authentication factor comprises a respective identifier of a respective user of the respective authentication device. The system further includes means for determining a probability that the respective user of each respective authentication device is a particular trusted user based on the received authentication factors. The system also includes means for comparing, by the server device, the probability to a threshold authentication probability. The system further includes, responsive to determining that the probability exceeding the threshold authentication probability, means for sending, to a client device, an authentication confirmation comprising an indication of the particular trusted user.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
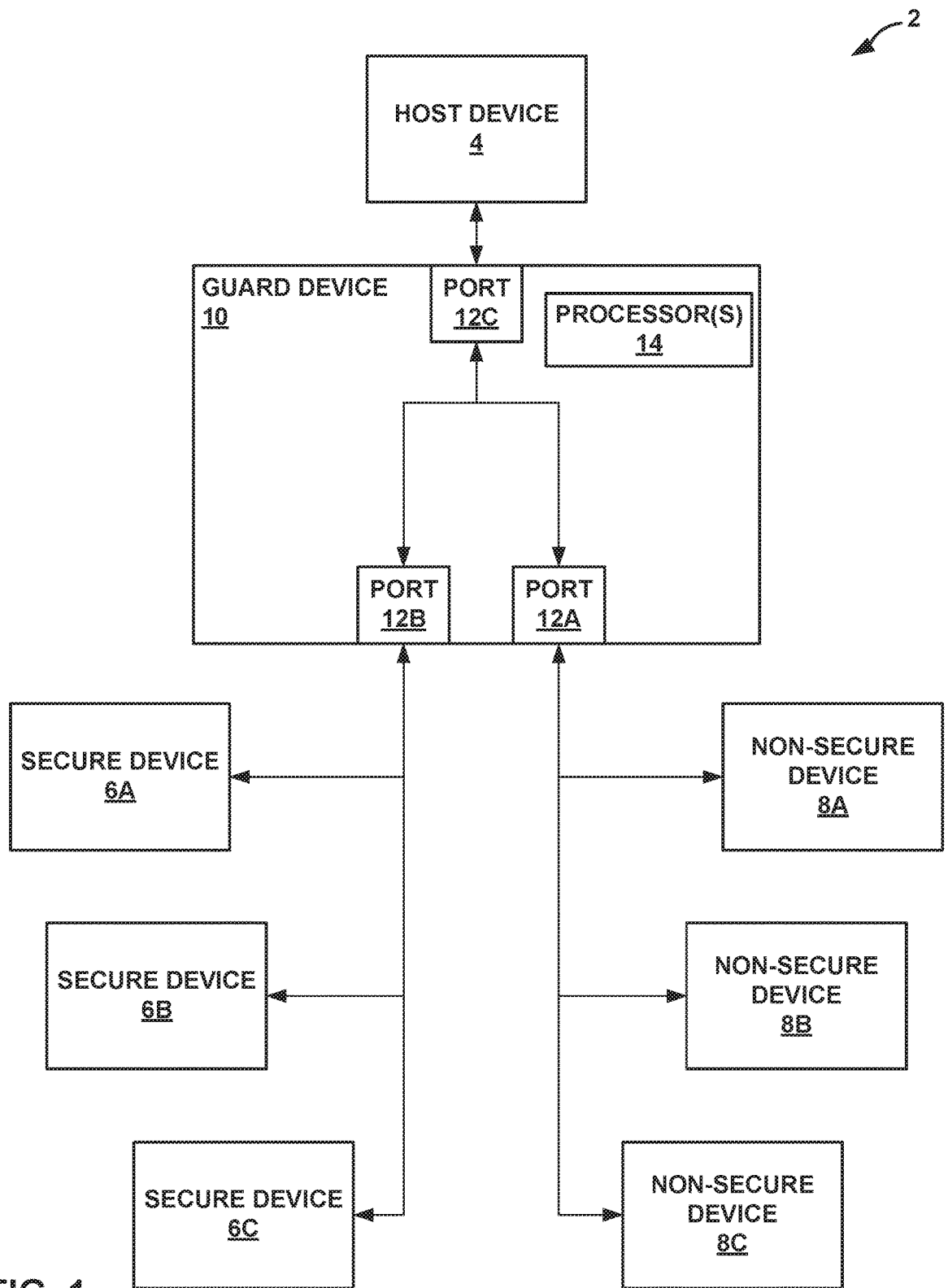
FIG. 1 is a block diagram illustrating an example of a guard device configured to receive data packets from both secure client devices and non-secure client devices and to forward the received data packets to a host device, in accordance with one or more techniques of this disclosure.

In general, this disclosure describes techniques for authenticating an identity of a user using a server device, a system of authentication devices, a guard device (e.g., a cross-domain communication device that may or may not include hub functionality), and at least one client device. At least three authentication devices from a group of three or more authentication devices, each of which are in a non-secure domain, may each create an authentication factor (e.g., a passcode, a signature, profile data, biometric information, or authentication data stored on a security device), either through user input or user analysis, for a user that is attempting to access the client device. A server device, such as a portable micro-server device in the vicinity of the client device, may receive the authentication factors in a secure domain. The server device may determine a probability that the respective user of each authentication device is a particular trusted user and compare the probability to a threshold authentication probability. Based on this comparison, the server device sends either an authentication confirmation or an authentication denial to the client device, which will grant or deny access to the user based on this result. While the techniques described herein generally refer to the server device as a separate device than the guard device or the client device, the server device may instead be integrated into either the guard device or the client device, enabling the respective device to perform the verification techniques described herein without adding an additional device to the overall system.

In cases where a user in the field (i.e., apart from a control center) is attempting to access a client device that operates in a secure domain, such as tactical networks with classified environments, authentication of the user may be required before access to the client device is granted. Even upon grant of access, the identity and security classification of the user may limit access to particular features of the client device, as opposed to unhindered use of the client device. Authentication devices may be added to the system to provide this needed authentication. However, if the authentication devices are also to be in the secure domain, each authentication device would have to undergo expensive and time-consuming modification to operate in such a manner. If the authentication devices are to be cheaper, off-the-shelf devices that operate in a non-secure domain, allowing communication between the authentication devices and the client device directly may lead to security issues and greater instances of hacking attempts. Further, if authentication is performed by the client device, a database of the authentication factors must be stored on the client device, as well as algorithms for performing the authentication. This may not be possible, depending on the type of the client device and the functional limitations of the client device (e.g., a radio device may not have designated long-term storage space or the software modules necessary for performing such authentication). Furthermore, the client device may not be approved to hold the classified data needed to perform the authentication.

As such, the techniques of this disclosure describe utilizing a micro-server device that receives authentication from a guard device (that may also act as a hub device) and performs the authentications steps. A micro-server may be any portable device or wearable device that may communicate or process data in a manner similar to a larger, stationary server device. By sending the authentication factors through the guard device, the micro-server may ensure safety of the data it is receiving from the authentication devices, at least one of which is in a non-secure domain. Further, the micro-server device may be particularly configured to store authentication factors for multiple users and perform authentication on numerous authentication devices, enabling the client device to perform with minimal alterations for the specific authentication required in tactical networks.

This disclosure further describes a guard device that is configured to receive data packets from both secured client devices and non-secured client devices. In situations where authentication devices, that may not be in a secure domain, send authentication factors to client devices in a secure domain, a guard device, such as the guard device described herein, may be used to enable communication of said non-secure authentication factors to the secure client device in a secure manner. In some instances, the guard device may send the data packets from the secured client devices straight to a secured host device, as secured client devices may be implicitly trusted within the overall system of devices in the information exchange. In other instances, the guard device may perform some preliminary processing of the secure data packets, such as determining a sender of the data packets or the type of contents within the data packets. For the data packets originating from the non-secured client devices, the guard device may first process the data packets to ensure the integrity of the received non-secure data packets. Generally, the guard device may process and route non-secure traffic according to some pre-defined guard process based on the particular non-secure source. For instance, the guard device may perform a virus scan and/or some other integrity check on the non-secure data packets prior to sending the non-secure data packets to the host device such that the guard device blocks unsafe data packets or infiltration attempts from outside devices being forwarded to the host device.

Other devices that may attempt to implement various guard functionality for a system may simply block all non-secured data from reaching the host device entirely. However, the non-secured data may still include critical information necessary for the host device. As such, blocking the data entirely may be detrimental. In other examples, the host device itself may analyze the non-secured data once it reaches the host device. However, due to the potential damaging nature of non-secured data, malicious or virus-laden data may damage the host device to the point of where the host device may be useless or compromised.

Rather than blocking all of the non-secured data or letting all of the non-secured data reach the host device, the techniques described herein may provide heightened one-way filtering of incoming data packets/streams received from non-secured client devices (e.g., transmission control protocol (TCP) data flows and user datagram protocol (UDP) data flows). Further, a single guard device may act as a hub device and interconnect multiple data sources, both secured and non-secured, across multiple ports to the secured host device. A single guard device also implies a single configuration interface. The guard device, for example, may be a computing device with a full central processing unit (CPU), one or more universal serial bus (USB) ports (e.g., 4), one or more Ethernet ports (e.g., 2), and an operating system or a micro-operating system (e.g., the evaluation assurance level (EAL) 7 secure level 4 (seL4) micro-kernel), although other examples of the guard device may include more or fewer ports, different protocols for the ports (e.g., Wi-Fi, Bluetooth, etc.), or a different CPU and/or operating system. The guard device of this disclosure may perform the techniques described herein regardless of the device type, vendor, or operating system used by the end-user host device.

FIG. 1 is a block diagram illustrating an example system 2 that includes guard device 10 configured to receive data packets from both secure client devices 6A-6C and non-secure client devices 8A, 8B, and 8C and to forward the received data packets to a host device 4, in accordance with one or more techniques of this disclosure. In the techniques of the current disclosure, the server device that performs the authentication techniques described herein may receive the authentication facts from authentication devices via a guard device, such as guard device 10. System 2 is shown to include host device 4, secure client devices 6A-6C (collectively, secure client devices 6), non-secure client devices 8A, 8B, and 8C (collectively, non-secure client devices 8), and guard 10. This specific arrangement of devices, however, is only a single example configuration of system 2. In other configurations, there may be more secure/non-secure client devices or less (as few as zero) secure/non-secure client devices operably connected to guard 10 than shown in FIG. 1.

Host device 4 is an end-user device (EUD) described below, for purposes of illustration only, as a tablet computer. However, in some examples, host device 4 may be a computerized watch (e.g., a smart watch), computerized eyewear, computerized headwear, other types of wearable computing devices, a smartphone, a personal digital assistant (PDA), a laptop computer, a media player, a television platform, an automobile navigation system, a digital camera, or any other type of mobile and/or non-mobile computing device that is configured to perform a media operation as described herein.

Secure client devices 6 may be any device configured to send data packets to guard 10 over a secured channel (e.g., a hard-wired connection or a closed/protected network connection) and further configured to operate in accordance with a trusted secure security classification, such as secret, top secret, classified, or protected. Examples of secure client devices 6 may include a secured radio device, a secured global positioning system device, any computing device configured to operate in accordance with an encryption protocol also used by host device 4, a computing device configured to utilize steganography to write a particular string of data within a data packet, any computing device that has been approved for secure status (e.g., an approved surveillance drone, an approved UAV, an approved video feed, an approved biometric sensor, etc.), or any other computing device configured to operate with some threshold level of security such that host device 4 may implicitly trust the data packets received from secure client devices 6.

Non-secure client devices 8 may be any device configured to send data packets to guard 10 over a non-secured channel (e.g., an open network or an unprotected network) or a channel with unknown security. Further, non-secure client device 8 may not be configured to operate in accordance with a trusted secure security classification or it may be unknown to guard 10 and host device 4 as to whether non-secure client devices 8 are configured to operate in accordance with a trusted secure security classification. Examples of non-secure client devices 8 may include a UAV, a general data producing device not configured to operate in accordance with a trusted security protocol, video and voice applications, anonymous cellular phones, landline telephones, anonymous Internet devices, any computing device that has not been approved for secure status (e.g., a non-approved surveillance drone, a non-approved video feed, a non-approved biometric sensor, etc.), biometric sensors, or any other untrusted or potentially unsafe computing device.

While described herein as "client" devices, any of secure client devices 6A-6C or non-secure client devices 8A-8C may be authentication devices, either in a secure domain or a non-secure domain. In accordance with the techniques described herein, at least three of these authentication devices, with at least one being in the non-secure domain, may send an authentication factor to guard device 10. In examples where guard device 10 is configured to do the authentication, guard device 10 may determine a probability that the respective user of each respective authentication device is a particular trusted user based on the received authentication factors and compare the probability to a threshold authentication probability. In other examples, such as where an external micro-server device performs the authentication process or where host device 4 performs the authentication process, guard device 10 may, after ensuring the integrity and safety of the authentication factors, forward the authentication factors to the external micro-server device or host device 4, which will determine a probability that the respective user of each respective authentication device is a particular trusted user based on the received authentication factors and compare the probability to a threshold authentication probability. After the device that performs the authentication process and verifies that the probability exceeds the threshold authentication probability, the device may send an authentication confirmation to host device 4, the authentication confirmation including an indication of the particular trusted user.

For the purposes of this disclosure, guard 10 may be any device capable of receiving data from and sending data to at least two computing devices (i.e., host device 4 and at least one of secure client devices 6 or non-secure client devices 8). Guard 10 may be configured to utilize one or more different communication protocols for receiving and sending the data packets, including Wi-Fi (e.g., the Institute of Electrical and Electronics Engineers (IEEE) 802.11 standard), the Bluetooth protocol, various radio frequency communication devices and waveforms, USB, the Ethernet industrial protocol, radio waves/frequencies, the Internet protocol suite, Java remote method invocation, dynamic data exchange, or any other communication protocol suitable for exchanging secure and non-secure data packets.

Guard 10 may include three or more ports 12A, 12B, and 12C (collectively, ports 12). Ports 12 may serve as an interface between guard 10 and other computers or peripheral devices (e.g., host 4, secure client devices 6, and non-secure client devices 8). In some examples, ports 12 may refer to a physical connection, and in other examples, ports 12 may refer to logical or wireless connections. Electronically, when ports 12 refer to a physical connection, several conductors where ports 12 and a physical cable contacts connect may provide a method to transfer signals between devices. In other examples, ports 12 may refer to a portion of guard 10 configured to wirelessly connect with other computing devices in order to exchange information and data packets/streams.

Guard 10 may further include one or more processors 14. One or more processors 8, in one example, are configured to implement functionality and/or process instructions for execution within guard 10. For example, processors 14 may be capable of processing instructions stored in a storage device of guard 10. Examples of processors 14 may include, any one or more of a microprocessor, a controller, a digital signal processor (DSP), an application specific integrated circuit (ASIC), a field-programmable gate array (FPGA), or equivalent discrete or integrated logic circuitry.

In accordance with the techniques of this disclosure, processors 14 of guard 10 may receive, via port 12A, a first data packet from non-secure client device 8A. For instance, non-secure client device 8A may be a data producing device not configured to operate in accordance with a trusted or secure protocol. For instance, a secure protocol may include the IPsec protocol or the encapsulating security payload (ESP) protocol, among other things. Conversely, the non-secure data producing protocols may include the real-time protocol (RTP) for voice or audio, the voice over internet protocol (VoIP), or the file transfer protocol (FTP), among other things. However, non-secure client device 8A may generate information that would be beneficial to transmit to host 4. As such, non-secure client device 8A may transmit the data packets to guard 10 via port 12A.

Processors 14 of guard 10 may also receive, via port 12B, a second data packet from secure client device 6A. For instance, secure client device 6A may be a radio that transmits data packets wirelessly to guard 10 over a channel that uses a trusted or secure protocol. Host 4 may request a status update from a user of secure client device 6A, and secure client device 6A may respond by transmitting the data packets to guard 10 via port 12B.

In some examples, based on the sender of the respective data packet, processor 14 may perform separate guard processes on the respective data packets. For instance, processors 14 may perform a first guard process on the first data packet based on the security classification of non-secure client device 8A (i.e., non-secure or untrusted) and perform a second guard process on the second data packet based on the security classification of secure client device 6A (e.g., a secure security classification, such as secret, top secret, classified, or protected). For the second guard process, in some instances, processors 14 may simply forward the second data packet to host 4 via port 12C. In other instances, for the second guard process, processors 14 may analyze contents of the second data packet to determine an identity of the sender of the second data packet or the type of contents in the second data packet prior to forwarding the second data packet to host 4 via port 12C. As the second data packet may come from a secure and trusted client device, processors 14 may refrain from determining an integrity of the received data and performing a virus scan operation on the second data packet. As described in greater detail below with respect to FIG. 2, the first guard process may include performing an integrity check and/or a virus scan, or, generally, a heightened filtering process.

Processors 14 of guard 10 may send, via port 12C, the first data packet from non-secure client device 8A and the second data packet from secure client device 6A to host 4. Port 12C may forward the respective data packets to host 4 either upon receipt of the respective data packets or after the respective data packets have been processed. In other words, port 12C may not necessarily forward the first data packet and the second data packet simultaneously, but instead forward the first data packet and the second data packet after processors 14 determines the respective data packet to be safe to forward to host 4 in the respective data packet's own respective processing loop. The timing with which processors 14 forward the first data packet is independent of the timing with which processors 14 forward the second data packet.

In some examples, processors 14 may simply forward the first data packet and the second data packet to host 4 upon receiving the respective data packets. In other examples, as described above, processors 14 may implement some form of guard process to evaluate the first data packet received from non-secure client device 8A. Upon determining that the first data packet meets a threshold level of integrity, processors 14 may forward the first data packet to host 4 via port 12C. In still other instances, processors 14 may process information certain information regarding the second data packet (i.e., sender information or content information) prior to forwarding the second data packet to host 4.

In some examples, processors 14 of guard 10 may receive an outgoing message to be sent to non-secure client devices 8 or secure client devices 6. For instance, if the outgoing message is intended for one of secure client devices 6, processors 14 of guard 10 may forward the outgoing message to the one of secure client devices 6 without restriction or with restrictions based on the respective trust level of the one of secure client devices 6. For instance, host 4 may attempt to send an ACK message, or an acknowledgement message that verifies the receipt of the incoming data packets, to non-secure client device 8A. However, in response to determining that the outgoing message contains secure information, processors 14 of guard 10 may refrain from sending the outgoing message to non-secure client device 8A so as to protect the integrity of the secured system. In other instances, however, processors 14 of guard 10 may scan the outgoing message to determine whether the outgoing message contains secure information that would be improper for a non-secure client device to receive. In response to determining that the outgoing message does not contain secure information, processors 14 of guard 10 may send the outgoing message to non-secure client device 8A via port 12A. Processors 14 may only send the outgoing messages to the non-secure client devices 8A and/or 8B when a security policy has been set up with approvals to send the such messages to the respective non-secure client devices.

In some other examples, rather than expecting host 4 to produce and send ACK messages, processors 14 may utilize a proxy module to produce an ACK message. If processors 14 still receive the ACK message from host 4, processors 14 may block the received ACK message and utilize a proxy module to produce an ACK instead. For instance, if the first data packet was part of a TCP conversation, processors 14 may utilize the proxy module to create an ACK message and send the ACK message to non-secure client device 8A. In creating a separate ACK message at processors 14, guard 10 may maintain a one-way communication between host 4 and the non-secure client device, as the non-secure client device will not receive any data created by host 4.

In other examples, processors 14 of guard 10 may prevent all outgoing traffic from reaching non-secure client device 8A. In such examples, processors 14 of guard 10 may receive an outgoing message to be sent to non-secure client device 8A. Upon determining that the intended recipient of the outgoing message is a non-secure client device (i.e., non-secure client device 8A), processors 14 of guard 10 may refrain from sending the outgoing message to non-secure client device 8A so as to protect the operation and safety of the secured system.

Guard 10 is one example of a device that may perform one-way guard functions to enable communication between devices in a non-secure domain (e.g., non-secure client devices 8) and a device in a secure domain (e.g., host 4). Although the techniques of this disclosure are described with respect to guard 10, any computing device that may perform similar one-way guard functions to process data packets received from a non-secure device and forward the non-secure data packets to a secure host device may be similarly utilized to perform the techniques of this disclosure. While authentication between devices is solved simply in the consumer world, the tactical world provides a more difficult authentication environment. For instance, wireless interfaces (e.g., wireless internet or radio frequencies) are disabled on host devices as part of military security regulations in an effort to reduce the cyber-attack surface of host 4 and to prevent unintended leakage of sensitive data from the secure host. Further, authentication devices may be non-secure devices (e.g., any of non-secure client devices 8), meaning that direct communication between the authentication devices and host 4 may be blocked or restricted. Guard 10, or any other device that may perform one-way guard functions, may enable the authentication devices to send authentication factors to host 4.

In some examples, host 4 may utilize biometric data received from guard 10 with the first data packet as verification for an identity of the user of host 4. For instance, a user of host 4 may be a trusted user (e.g., a user within the same organization or a known user having a particular level of security clearance) that is seeking to provide authentication to host 4 in order to gain access to one or more applications on host 4. In some instances, if host 4 is authenticating the user in a hostile situation or a situation where the user must access host 4 very quickly, host 4 may be unable to perform certain authentication processes due to the unavailability of certain authentication factors (e.g., the user is wearing gloves and unable to provide touch input on host 4, or voice authentication is unavailable due to extraneous environmental noise) or the length of time it takes to produce the authentication factor. Further, the various authentication devices may be non-secure devices (e.g., any of non-secure client devices 8), complicating the exchange of data between the authentication device and host 4. Instead, the trusted user may be equipped with biometric sensors (e.g., an electrocardiogram (ECG) monitoring bracelet) to verify the trusted user's identity. An ECG has five peaks and troughs, which are known as the PQRST pattern. An elevated heartbeat only alters the frequency of the pattern, but does not change the shape of an ECG or the pattern. The PQRST pattern also may remain the same as the person ages.

The trusted user may have a known PQRST pattern for their ECG stored in memory on host 4. When the trusted user is attempting to transmit data to host 4 via guard 10 and their non-secure device, the biometric sensors (e.g., the ECG monitoring bracelet) may take an ECG measurement of the trusted user. The biometric sensors may then transmit the ECG to guard 10, either itself or via a Bluetooth connected transmitter device, which then forwards the measurement to host 4 after performing a one-way guard process on the received data packets. If the ECG matches the stored ECG for the trusted user, the host device may have access to information related to that user, much in the same way as different personas are used when logging into shared devices. The ECG bracelets themselves also provide second factor authentication, using gestures, if desired. This information could all be used by host 4 to verify that the user transmitting the data is actually the trusted user.

The ECG authorization may be constant over a period of time. For instance, the biometric sensors may transmit constant ECG information to guard 10 along with the data packets for the non-trusted client device, which is forwarded to host 4. As long as the ECG information continues to match the stored ECG information, host 4 may approve the integrity of the received data packets. If the ECG information does not match, host 4 may determine that the trusted user may have been compromised and deny the received data packets.

The ECG authorization (with or without the additional gestures) may also be utilized as a password for accessing the host device. The host device may constantly confirm that the band is connected (e.g., by receiving data from the band).

If the bracelet is taken off, or the user connection is terminated (e.g., by going out of range), the authentication fails, and the host device would automatically lock. This ensures that the end user is who she/he claims to be, and the user has not changed. As soon as the band is out of range, or loses its connection, the host device may lock.

In some instances, the biometric sensors themselves may perform the verification, sending a data packet that identifies the user of the biometric sensors to guard 10 via a low emission radio beacon. Guard 10 may then forward the data packet to the host device. The host device could be configured to store information regarding multiple users. As such, if a medic were to control the host device and come across a wounded user who is also wearing the biometric sensors, the medic could access information about the wounded user using the biometric sensors as their identification. If each user were to wear some type of transmitting beacon, storing just basic information needed for treatment (i.e. name and serial number, or some form of encrypted ID), the database of information stored would be minimal. The application accessed by the medic may survey for beacons. The application executing on the host device would receive a beacon, identify the user, and synchronize with a local database.

While biometrics may be one example of ways that a user may access host device 4, host device 4 and guard 10 may utilize other devices and/or techniques to enable access to one or more applications stored on host device 4. In some examples, guard 10 may forward authentication factors received from various authentication devices (e.g., any of non-secure client devices 8) to a local server device. The local server device may verify an identity of a user of host 4. The local server device may validate and report the authenticity/identity status of users and their platforms using a web of wearable authentication devices, sensors and software and automatically adjust the level of communications allowed from an endpoint based on this information. Specifically, the local server device may receive at least three different authentication factors from respective authentication devices (e.g., any of non-secure client devices 8) to perform the multi-factor authentication process. Some of the received authentication factors may include multiple factors or signatures (e.g., the local server device may analyze a spoken password both for vocal characteristics and the content of the spoken phrase). In some instances, the local server device may select a subset of the received authentication factors that provide the best chance for user identification and analyze only those authentication factors in the identification process.

The techniques described herein may accommodate authentication of single users as well as a group of ad hoc users, while blocking others (i.e., enable identity based authentication as well as role-based authentication). Traditionally, this is accomplished using an authentication server operated by the enterprise within a remote facility. In a communication challenged tactical environment subjected to disconnected operations, reach-back to a backend server may not always be possible. These techniques overcome this problem using a fully distributed web of wearable authentication micro-servers (e.g., any of secure client devices 6) in the secure domain to provide mission assured authentication.

The local server (e.g., any of secure client devices 6) may use input from multiple sensors within vehicles, mounted outside of vehicles, and carried on users. Some options for these sensors include a voice recognition sensor, a global positioning system, a shoe tap input sensor, a finger tap input sensor, a hand geometry sensor, a hand grip sensor, a fingerprint sensor, an electrocardiogram (ECG) sensor, an ear print sensor, a radio frequency identification tag, a proximity sensor, a password entry device, a radio device, a gait sensor (local and remote), or a keystroke analyzer device. At least three authentication devices may produce one or more of a passcode, signature, profile data, biometric information, or other authentication data that can be stored on a security device. These sensors may connect to a local server device, that may be wearable, or an authentication micro-server through wired and wireless connections creating a web of sensors which feed the device with a variety of authentication factors to be used to perform multi-factor authentication.

This web of sensors provides inputs to the local server device. The local server device collects inputs then compares them against existing known signatures, prints, and profiles contained on the local server device and on nearby cloud servers (within a local mission network) to determine a probability that a person or vehicle are still under control and are who they represent. In some instances, the local server device may also send the inputs to a remote server device for further analysis and confirmation. The local cloud servers contain limited data for a smaller group of users, while remote cloud servers would be able to contain many more profiles and signatures. These profiles and signatures allow for ad hoc users and groups to authenticate dynamically as mission realities change. By including redundancy with low network overhead to counter falsified or hacked signatures, an adversary might be able to compromise a single or small number of units, but not all units, and eventually the local server device redundancy will find discrepancies.

In addition to sensors for positive identification of soldiers and vehicles, sensors may also determine liveness (e.g. heart rate, body temperature, respiratory) as well as detect unknown people. The local server device (or any other device configured to perform the authentication techniques described herein) may adjust the risk probabilities in such a situation. For example, a proximity sensor (and/or occupancy sensor or multiple motion and proximity sensors around a vehicle) could be used to count the number of people nearby, then compare to known radio frequency identifications (RFIDs) of coalition soldiers to count a number of possible unknown people (vs. valid RFIDs or valid/known gait profiles). As the number of unknown people increases, the risk of compromise increases and a higher authentication threshold may be required. In some instances, this number of unknowns can be conveyed to remote users for situational awareness.

In accordance with the techniques of this disclosure, the local server device may receive, in a secure domain and via guard 10, an authentication factor from at least three authentication devices of a group of three or more authentication devices. At least one authentication device in the group of three or more authentication devices is in a non-secure domain. Further, each respective authentication factor comprises a respective identifier of a respective user of the respective authentication device. The local server device may determine a probability that the respective user of each respective authentication device is a particular trusted user and compare the probability to a threshold authentication probability based on the received authentication factors. Responsive to determining that the probability exceeds the threshold authentication probability, the local server device may enable access to one or more applications on host 4 by sending an authentication confirmation to host 4. In some instances, in addition to performing the authentication locally, the local server may also send the received authentication factors to a remote server for additional confirmation and only enable access to the applications on host 4 once the additional confirmation is received from the remote server.

Conversely, responsive to determining that the probability does not exceed the threshold authentication probability, in some instances, the local server device may disable the access to one or more applications on host 4. In other instances, responsive to determining that the probability does not exceed the threshold authentication probability, the local server may attempt to send the authentication factors and a request to verify the identity of the respective user of the respective authentication device to a remote server and receive one of the identity of the respective user of the respective authentication device or an indication that an untrusted user attempted to gain access to host 4. The local server device may also disable a login credential for the particular user if the probability does not exceed the threshold authentication probability.

These techniques may use multiple identification parameters that, in combination, speed access to host 4 while ensuring reliable, strong authentication. Biometric sensors that may be utilized with these techniques include a voice recognition sensor, a global positioning system, a shoe tap input sensor, a finger tap input sensor, a hand geometry sensor, a hand grip sensor, a fingerprint sensor, an electrocardiogram sensor, an ear print sensor, a radio frequency identification tag, a proximity sensor, a password entry device, a radio device, a gait sensor, or a keystroke analyzer device. Each authentication device may produce one or more of a passcode, a signature, profile data, authentication data that may be stored on a security device, or biometric information. The authentication factors may also include information that identifies a user as being part of a particular group, and the access granted to the user is in line with general permissions granted to users of that group (e.g., the user is a medic, granting them access to medical information).

The local server device may intermittently request updates from each of the authentication devices in order to continually verify the identity of the user accessing host 4. In such instances, after sending the authentication confirmation to the client device, the local server device may send, to each of the authentication devices, a request for an updated authentication factor. After receiving the updated authentication factors, the local server device may repeat the above authentication process.

In other examples, host device 4 may itself store the data needed to verify the identity of the prospective user. As such, host 4 may quickly authenticate a user based on authentication factors received from a plurality of authentication devices via guard 10. Host device 4 may request input of a strong password (or combination of authentication factors) at power-on. After periods of inactivity that turn off a screen of host 4 to conserve battery and invoke the screen lock, host 4 may require re-authentication before enabling access to one or more applications on host 4. In some instances, host 4 may examine a combination of other authentication factors, other than the strong password and make a decision to unlock the screen and enable application access internally based on the results of these other authentication factors. Examples of these additional authentication factors include biometric signatures such as heart monitors (ECG fingerprinting), voice recognition, or stride (i.e., individual "gait" or walk/run pattern) analysis. In general, the authentication factors may be dynamic in the sense that the specific combination of authentication factors required for enabling access to host 4 may be configurable and reconfigurable. These biometric signatures can be augmented with additional authentication factors, such as digital certificates that are stored on the user's radio frequency identification (RFID) tags. By using multi-factor authentication, host 4 may enable access quickly, easily, and with high confidence that the right user is gaining access to host 4. Further, since the authentication factors are configurable and reconfigurable, host 4 may be configured to utilize optimal mission-specific authentication factors.

As such, guard 10 may include a software-based data diode (or any other device or software that may perform one-way guard functions described herein) and an embedded processor that incorporates its own low-power radio frequency (RF) transceiver that can communicate with biometric sensors. By only letting data travel wirelessly from the biometric sensor (low side) to guard 10 and then to host 4 over a wired connection, and by ensuring that no data can traverse the opposite path, these techniques provide a way to incorporate non-secure biometric sensors for fast user authentication in a secure fashion that is acceptable to cyber-security professionals.

In accordance with the techniques of this disclosure, host 4 may receive, in a secure domain and via guard 10, an authentication factor from at least three authentication devices of a plurality of authentication devices. At least one authentication device in the plurality of authentication devices is in a non-secure domain. Further, each respective authentication factor comprises a respective identifier of a respective user of the respective authentication device. Host 4 may determine whether the respective user of each respective authentication device is a particular trusted user based on the received authentication factors. Responsive to determining that the respective user of each respective authentication device is the particular trusted user, host 4 may enable access to one or more applications on host 4. Conversely, responsive to determining that the respective user is not the particular trusted user, host 4 may disable the access to the one or more applications on the computing device.

These techniques may use multiple identification parameters that, in combination, speed access to host 4 while ensuring reliable, strong authentication. Biometric sensors that may be utilized with these techniques include a voice recognition sensor, a global positioning system, a shoe tap input sensor, a finger tap input sensor, a hand geometry sensor, a hand grip sensor, a fingerprint sensor, an electrocardiogram sensor, an ear print sensor, a radio frequency identification tag, a proximity sensor, a password entry device, a radio device, a gait sensor, or a keystroke analyzer device. Each authentication device may produce one or more of a passcode, data stored on a security device, or biometric information.

Host 4 may determine that the respective user of each respective authentication device is the particular trusted user by comparing each received authentication factor to a respective baseline authentication factor for the particular trusted user and determining that the respective user of each respective authentication device is the particular trusted user if each received authentication factor is within a threshold percentage of the respective baseline authentication factor. In some examples, the number of authentication factors required for authentication may be defined by a remote officer. In some instances, the number may be defined by receiving, from a remote computing device, an indication of a minimum number of authentication factors to be received by host 4. The authentication process may then additionally include determining that a majority of the received authentication factors are within the threshold percentage of the respective baseline authentication factor. In other instances, the number may be defined by receiving an indication of a number of authentication factors required to enable access to host 4. The authentication process may then additionally include determining that a number of received authentication factors is greater than or equal to the number of authentication factors required to enable access to the computing device.

Figure 2:
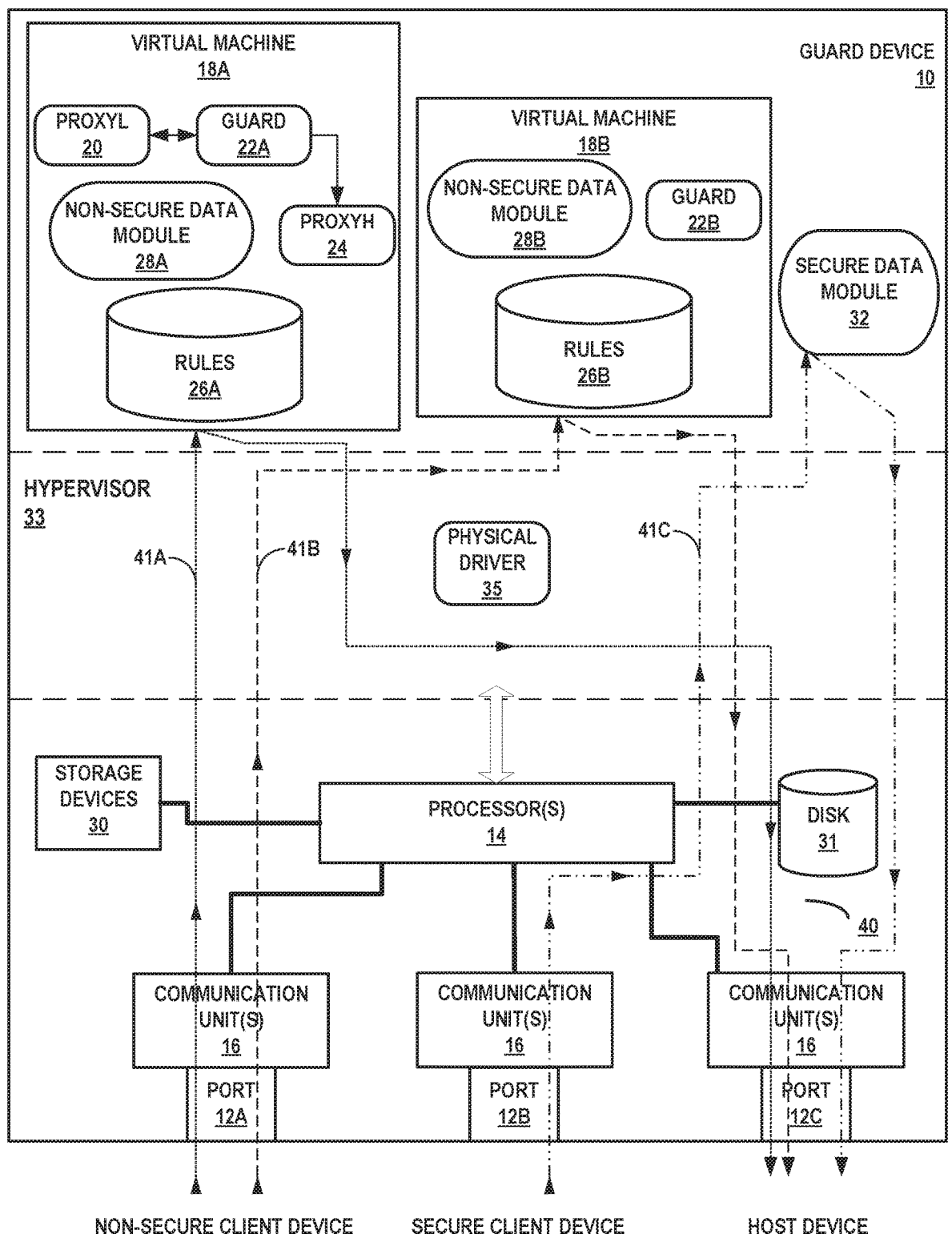
FIG. 2 is a block diagram illustrating an example guard device of FIG. 1 in more detail.

FIG. 2 is a block diagram illustrating a detailed example of guard device 10 configured to receive data packets from both secure client devices and non-secure client devices and to forward the received data packets to a host device, in accordance with one or more techniques of this disclosure. In the techniques of the current disclosure, the server device that performs the authentication techniques described herein may receive the authentication facts from authentication devices via a guard device, such as guard device 10. FIG. 2 illustrates some particular examples of guard 10, and many other examples of guard 10 may be used in other instances and may include a subset of the components included in example guard 10 or may include additional components not shown in FIG. 2.

For example, guard 10 may include a battery to provide power to the components of guard 10, or guard 10 may include more ports than three (e.g., four or more ports). Similarly, the components of guard 10 shown in FIG. 2 may not be necessary in every example of guard 10. For example, in some configurations, guard 10 may not include one or both of virtual machines 18A and 18B, meaning that only a single virtual machine may be included for handling data packets received from a non-secure source. However, for ease of illustration, guard 10 is shown in FIG. 2 to include both virtual machines 18A and 18B. As shown in the example of FIG. 2, guard 10 includes one or more processors 14, one or more communication units 16, virtual machines 18A and 18B executable by one or more processors 14, and one or more storage devices 30.

One or more storage devices 30 of guard 10 include virtual machines 18A and 18B and secure data module 32. One or more storage devices 30 may be configured to store information within guard 10 during operation. Storage device 30, in some examples, is described as a computer-readable storage medium. In some examples, storage device 30 is a temporary memory, meaning that a primary purpose of storage device 30 is not long-term storage. Storage device 30, in some examples, are described as volatile memories, meaning that storage device 30 does not maintain stored contents when the computing device is turned off. Examples of volatile memories include random access memories (RAM), dynamic random access memories (DRAM), static random access memories (SRAM), and other forms of volatile memories known in the art. In some examples, storage device 30 is used to store program instructions for execution by processors 8.

Storage devices 30, in some examples, also include one or more computer-readable storage media. Storage devices 30 may be configured to store larger amounts of information than volatile memory. Storage devices 30 may further be configured for long-term storage of information. In some examples, storage devices 30 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Disk 31 represents computer readable storage media that includes volatile and/or non-volatile, removable and/or non-removable media implemented in any method or technology for storage of information such as processor-readable instructions, data structures, program modules, or other data. Computer readable storage media includes, but is not limited to, random access memory (RAM), read-only memory (ROM), EEPROM, flash memory, CD-ROM, digital versatile discs (DVD) or other optical storage, magnetic cassettes, magnetic tape, magnetic disk storage or other magnetic storage devices, or any other medium that can be used to store the desired information and that can be accessed by processor 14.

Communication channels 40, represented by the solid lines in FIG. 2, may interconnect each of (or some subcombination of) the components 14, 16, 12A, 12B, 12C, and 30 for inter-component communications (physically, communicatively, and/or operatively). In some examples, communication channels 40 may include a system bus, a network connection, an inter-process communication data structure, or any other method for communicating data. The communication channels for a particular set of components may be isolated from another set of components.

Virtual data paths 41A-41C, represented by the dotted lines of various patterns, represent virtual connections within guard 10. For instance, data packets may be received by one of ports 12A-12C and be processed by one of virtual machines 18A-18B or secure data module 32. After being processed, the data packets may be output to a different device via another one of ports 12A-12C. Although each of virtual data paths 41A-41C is shown as being received by one of ports 12A or 12B and being output by port 12C, each of the data paths may be reversed. In other words, port 12C may receive data from the host device to be output to non-secure client devices or secure client devices via ports 12A or 12B.

One or more communication units 16 of guard 10 may communicate with external devices, such as a server device, a host device, secure client devices, and/or non-secure client devices, via one or more wired and/or wireless networks by transmitting and/or receiving network signals on the one or more networks. Communication units 16 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, guard 10 utilizes communication units 16 to wirelessly communicate with another computing device that is operably coupled to guard 10, such as host device 4, secure client devices 6, and/or non-secure client devices 8 of FIG. 1.

In some examples, communication units 16 may include a sufficient number of communication units such that each of ports 12A-12C connects to components in guard 10 through a respective communication unit. In other words, port 12A may utilize a first one of communication units 16 to receive data packets from an outside computing device and to send the received data packets to the correct units for processing. In other examples, the respective ports 12A-12C may be configured to automatically send the received packets to the correct units on its own. In other words, communications channels for different sets of components can be isolated.

One or more processors 14, in one example, are configured to implement functionality and/or process instructions for execution within guard 10. For example, processors 14 may be capable of processing instructions stored in storage device 30. Examples of processors 14 may include, any one or more of a microprocessor, a controller, a digital signal processor (DSP), an application specific integrated circuit (ASIC), a field-programmable gate array (FPGA), or equivalent discrete or integrated logic circuitry.

Guard 10 executes a hypervisor 33 to manage virtual machines 18. Example hypervisors include Kernel-based Virtual Machine (KVM) for the Linux kernel, Xen, ESXi available from VMware, Windows Hyper-V available from Microsoft, and other open-source and proprietary hypervisors. Hypervisor 33 may represent a virtual machine manager (VMM). Hypervisor 33 includes a physical driver 35 to use the physical function provided by a network interface card.

Each of virtual machines 18 may include a virtual driver presented directly into the virtual machine guest operating system, effectively bypassing hypervisor 33 to offer direct communication between communication units 16 and the virtual machine. This may reduce hypervisor 33 overhead involved with software-based, vSwitch implementations.

Guard 10 may include virtual machines 18A and 18B (collectively, virtual machines 18), and secure data module 32. Each of virtual machines 18A and 18B may include a respective non-secure data module 28A and 28B. Modules 28A, 28B, and 32 may perform operations described using software, hardware, firmware, or a mixture of hardware, software, and firmware residing in and/or executing at guard 10. Guard 10 may execute modules 28A, 28B, and 32 with one or more processors. Guard 10 may execute modules 28A, 28B, and 32 as a virtual machine executing on underlying hardware. Modules 28A, 28B, and 32 may execute as a service or component of an operating system or computing platform. Modules 28A, 28B, and 32 may execute as one or more executable programs at an application layer of a computing platform. Modules 28A, 28B, and 32 may be otherwise arranged remotely to and remotely accessible to guard 10, for instance, as one or more network services operating at a network in a network cloud. In other words, modules 28A, 28B, and 32 may not be executing at guard 10. Instead, modules 28A, 28B, and 32 may be executing at a remote computing system (e.g., a server).

Virtual machines 18 and secure data module 32 may be stored in long-term storage, such as storage 30. However, when virtual machines 18 or secure data module 32 are executed by processor 14, processor 14 may read virtual machines 18 or secure data module 32 into volatile memory, such as disk 31. Virtual machines 18 or secure data module 32 may be stored in disk 31 throughout processor 14's execution of virtual machines 18 or secure data module 32.

Virtual machines 18 may be an emulation of a computer system. Virtual machines 18 may be based on computer architectures and provide functionality of a physical computer. Virtual machines 18 may be implemented in guard 10 using specialized hardware, software, or a combination thereof. Virtual machines 18 may be process virtual machines designed to execute the techniques described herein in a platform-independent environment. Specifically, each of virtual machines 18 may be designed to execute the guard and filtering techniques for data packets received from a non-secure client device. Although shown as virtual machines, virtual machines 18A and/or 18B may instead be containers. In such instances, a kernel of hypervisor 33 may allow for multiple, distinct virtualization engines that may enable the performance of the techniques described herein. Each of virtual machines 18A and 18B may include various hardware or software components to perform the techniques of this disclosure. These components are described in greater detail below.

In accordance with the techniques of this disclosure, processors 14 of guard 10 may receive, via port 12A, a first data packet from a non-secure client device. For example, the non-secure client device may be a UAV attempting to send data (e.g., a full motion video TCP stream) to the host device. The UAV may not be configured to operate in accordance with a trusted or secure protocol. However, the UAV may still generate information that would be beneficial to transmit to host 4. As such, the UAV may transmit the data packets associated with the TCP stream to guard 10 via port 12A. In examples where guard 10 includes virtual machine 18A, the first data packet may generally follow path 41A, i.e., the first data packet may be received by port 12A, analyzed using virtual machine 18A, and output via port 12C. In other examples where guard 10 includes virtual machine 18B, the first data packet may generally follow path 41B, i.e., the first data packet may be received by port 12A, analyzed using virtual machine 18B, and output via port 12C.

Processors 14 of guard 10 may also receive, via port 12B, a second data packet from a secure client device. For instance, the secure client device may be a global positioning system (GPS) device that transmits data packets that include various locations to guard 10 over a secure channel. Host 4 may request a status update from a user of the GPS with regards to the location of the GPS, and the GPS may respond by transmitting the data packets to guard 10 via port 12B. The second data packet, upon being received at port 12B, may generally follow path 41C within guard 10, i.e., the second data packet may be received by port 12B, analyzed using secure data module 32, and output via port 12C.

In some examples, based on the sender of the respective data packet, processor 14 may perform separate guard processes on the respective data packet. For instance, non-secure data modules 28A and/or 28B may receive the non-secure data packet from port 12A and perform a first guard process on the first data packet based on the security classification of the UAV (i.e., non-secure or untrusted) and secure data module 32 may perform a second guard process on the second data packet based on the security classification of the GPS (e.g., a secure security classification, such as secret, top secret, classified, or protected). For the second guard process, in some instances, secure data module 32 may simply forward the second data packet to the host device via port 12C. In other instances, for the second guard process, secure data module 32 may analyze contents of the second data packet to determine an identity of the sender of the second data packet or the type of contents in the second data packet prior to forwarding the second data packet to the host device via port 12C. As the second data packet may come from a secure and trusted client device, secure data module 32 may refrain from determining an integrity of the received data and performing a virus scan operation on the second data packet.

For the first guard process, non-secure data module 28A or 28B may execute the respective guard process 22A or 22B to perform an integrity check on the first data packet based at least in part on a type of connection between guard 10 and the non-secure client device and a data type of the first data packet. In other words, the data packet may have a different structure depending on the type of data stored within the data packet and the protocol used to transmit the data packet to guard 10. As such, the specific method for determining the integrity of the first data packet may vary based on the expected structure of the first data packet. Non-secure data module 28A or 28B may determine an expected structure of the first data packet based at least in part on type of connection between guard 10 and the non-secure client device and the data type of the first data packet. Non-secure data module 28A or 28B may also determine an actual structure of the first data packet and compare the actual structure with the expected structure. If non-secure data module 28A or 28B determines that the actual structure of the first data packet matches the expected structure of the first data packet, non-secure data module 28A or 28B may determine that the first data packet passes the integrity check and send the first data packet to the host device via port 12C. Conversely, if non-secure data module 28A or 28B determines that the actual structure of the first data packet does not match the expected structure of the first data packet, non-secure data module 28A or 28B may determine that the first data packet fails the integrity check and block the first data packet from reaching the host device.

Part of the integrity check may include non-secure data modules 28A and 28B determining that the actual structure of the first data packet matches an expected structure based on the type of data stored within the data packet and the protocol used to transmit the data packet to guard 10. For instance, if the UAV sends the TCP stream using Wi-Fi, non-secure data modules 28A and 28B may expect the first data packet to have a particular structure with particular bitfields filled out in particular ways. Non-secure data modules 28A and 28B may determine that the first data packet passes the integrity check if the bitfields match the expected structure.

Another part of the integrity check may include non-secure data modules 28A and 28B performing a virus scan operation on the first data packet. The virus scan operation may include comparing certain values within the data packet to known virus or malware structures. If non-secure data modules 28A and 28B determine that the first data packet contains a virus or malware, then non-secure data modules 28A and 28B may block the first data packet from reaching the host device. Conversely, if non-secure data modules 28A and 28B determines that the virus scan operation shows no harmful data in the first data packet, non-secure data modules 28A and 28B may forward the first data packet to the host device via port 12C.

Secure data module 32 and non-secure data modules 28A and 28B of guard 10 may send, via port 12C, the first data packet and the second data packet to the host device. The respective data modules may forward the respective data packets to host device 4 either upon receipt of the respective data packets or after the respective data packets have been processed. In other words, the respective data modules may not necessarily forward the first data packet and the second data packet simultaneously, but instead forward the first data packet and the second data packet after the respective data modules determines the respective data packet to be safe to forward to the host device in the respective data packet's own respective processing loop. The timing with which non-secure data modules 28A and/or 28B forward the first data packet is independent of the timing with which secure data module 32 forwards the second data packet.

In some examples, modules 28A, 28B, and 32 may simply forward the first data packet and the second data packet to the host device upon receiving the respective data packets. In other examples, as described above, modules 28A and 28B may implement some form of guard process to evaluate the first data packet received from the non-secure client device. Upon determining that the first data packet meets a threshold level of integrity, non-secure data modules 28A and 28B may forward the first data packet to the host device via port 12C. In still other instances, secure data module 32 may process certain information regarding the second data packet (e.g., sender information or content information) prior to forwarding the second data packet to the host device.

In some examples, non-secure data module 28A or 28B of guard 10 may receive an outgoing message to be sent to the non-secure client device. For instance, the host device may attempt to send an ACK message to the UAV. In some instances, non-secure data modules 28A and 28B of guard 10 may prevent all outgoing traffic from reaching non-secure client device 8A. In such examples, non-secure data module 28A or 28B of guard 10 may receive an outgoing message to be sent to the non-secure client device. Upon determining that the intended recipient of the outgoing message is a non-secure client device (e.g., the UAV), non-secure data module 28A or 28B of guard 10 may refrain from sending the outgoing message to the non-secure client device so as to protect the integrity of the secured system.

In other examples, guard 10 may forward the ACK message to the non-secure client device. Prior to forwarding the ACK message, non-secure data module 28A or 28B of guard 10 may scan the outgoing message to determine whether the outgoing message contains secure information that would be improper for a non-secure client device to receive based on various security protocols that guard 10 must operate within. In response to determining that the outgoing message does not contain secure information, non-secure data module 28A or 28B of guard 10 may send the outgoing message to the non-secure client device via port 12A. However, in response to determining that the outgoing message contains secure information, non-secure data module 28A or 28B of guard 10 may refrain from sending the outgoing message to the non-secure client device so as to protect the integrity of the secured system.

In some other examples, rather than waiting for the host device to produce and send ACK messages, virtual machine 18A may utilize proxy modules 20 and 24 to produce an ACK message. If non-secure data module 28A or 28B still receives the ACK message from the host device, guards 22A or 22B may block the received ACK message and utilize a proxy module to produce an ACK instead. For instance, if the first data packet was part of a TCP message, non-secure data module 28A may utilize the proxy modules 20 and 24, as described below, to create an ACK message and send the ACK message to the non-secure client device. By enabling guard 10 to create the ACK messages, outgoing communication from the host device to the non-secure client device is further limited or prevented. In creating a separate ACK message at ProxyL 20, guard 10 may maintain a one-way communication between the host device and the non-secure client device, as the non-secure client device will not receive any data created by the host device.

Depending on the final needs and requirements of the solution, both virtual machines 18A and 18B may be used as configurable options in addition to more or different types of flow controls. In the example of FIG. 2, virtual machine 18A uses two proxies 20 and 24, a high-side Proxy (e.g., ProxyH 24, or a proxy module located on the host-side of guard 22A) and a low-side proxy (e.g., ProxyL 20, or a proxy module located on the client-side (or low side) of guard 22A). Non-secure data module 28A may execute each of these proxies 20 and 24 to mimic or block the reverse packet flow in a TCP connection when no high to low traffic is required. A TCP application on the low side may expect ACKs and various feedback, including handshaking information, from the ultimate host device. ProxyL 20 may mimic or create these ACK messages as if ProxyL 20 were the actual endpoint, thus completing the data exchange loop needed for a full TCP connection. The TCP packets are then wrapped or modified to be user diagram protocol (UDP) packets and sent into the guard process where the flow is validated according to the configured flow type rules. Guard 22A may execute a guard process before ProxyL 20 handles the TCP connection. ProxyH 24 receives the ACKs and various TCP feedback and drops all traffic. ProxyH 24 may also receive the UDP packets from guard 22A and convert the UDP packets into TCP packets to forward on to an app on the host device.

Virtual machine 18B shows a simpler filtering technique that only includes guard 22B and does not mimic the TCP ACKs. In this example, traffic may flow both from the non-secure client device to the host device and from the host device to the non-secure client device. As such, the host device may generate the TCP ACK messages, which guard 10 may forward to the non-secure client device. Guard 22B may implement the same or more virus detection, deep packet inspection and other safeguards guard 22A.

In some examples, the cross-domain system in FIG. 2 may be implemented with or without virtual machines 18A and 18B. Virtual machines 18 may isolate the "low" traffic and "low" network interfaces from the rest of guard 10. However, other implementations of the functionality of each of virtual machines 18 may be utilized to perform the techniques of this disclosure.

Figure 3:
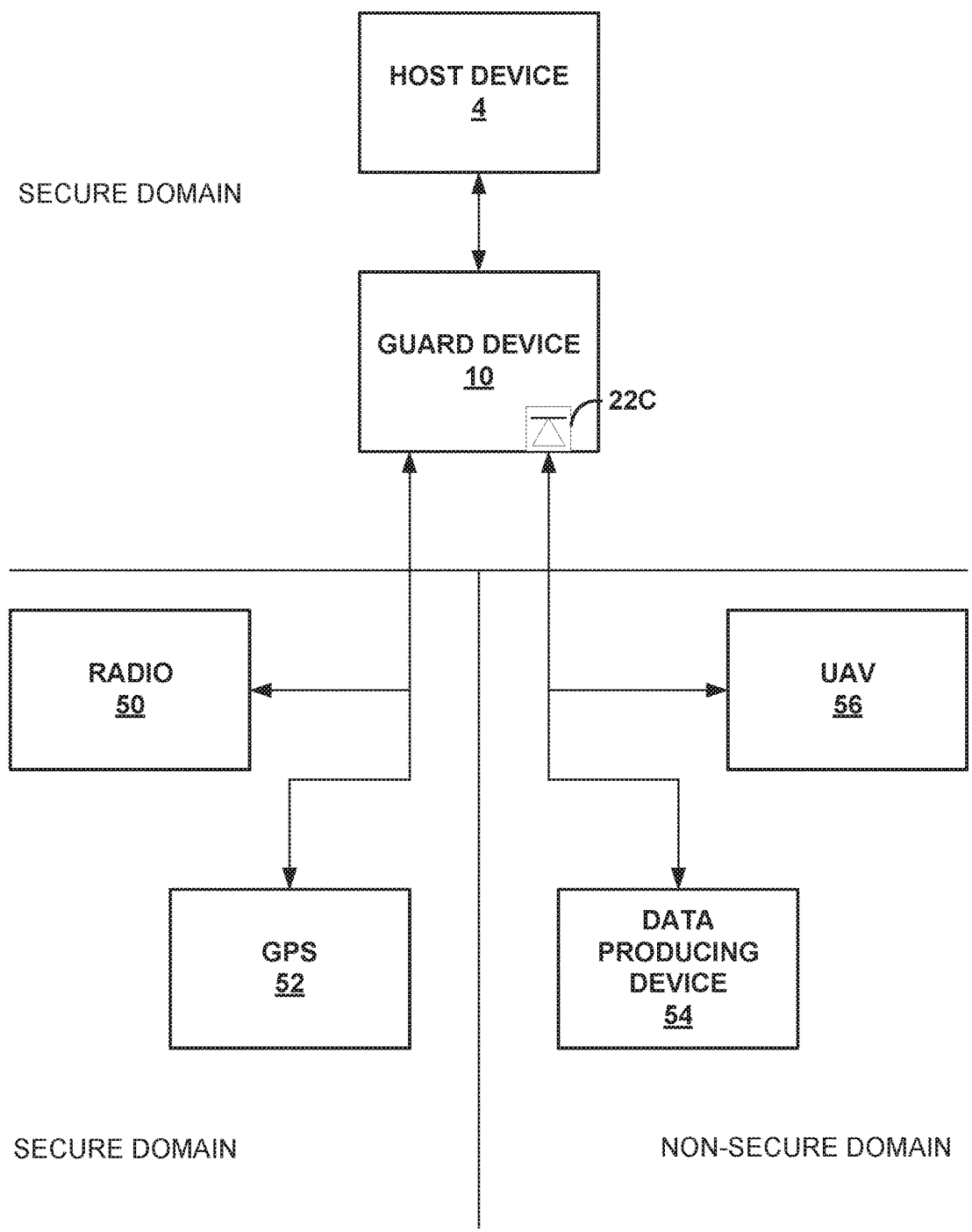
FIG. 3 is a block diagram illustrating an example system that includes a guard device configured to block outgoing communications to the non-secure client devices, in accordance with one or more techniques of this disclosure.

FIG. 3 is a block diagram illustrating an example system that includes guard device 10 configured to receive data packets from both secure client devices 50 and 52 and non-secure client devices 54 and 56, forward the received data packets to host device 4, and block outgoing communications to non-secure client devices 54 and 56, in accordance with one or more techniques of this disclosure. The techniques of FIG. 3 may be performed by one or more processors of a computing device, such as guard 10 illustrated in FIG. 1 and/or FIG. 2. For purposes of illustration only, the techniques of FIG. 3 are described within the context of guard 10 of FIG. 1, although computing devices having configurations different than that of guard 10 may perform the techniques of FIG. 3.

One option for controlling the outgoing traffic to non-secured client devices 54 and 56 is for guard 22C (similar to guards 22A and 22B of FIG. 2) in guard 10 to control the outgoing traffic from guard 10 to non-secured client devices 54 and 56. In this option, guard 22C may be implemented as part of guard 10 or operably connected to guard 10 and may allow general traffic to flow in only one direction (i.e., from the non-secure client devices 54 and 56 to guard device 10). In one instance, the data flow being in only one direction is absolute and all outgoing data from guard device 10 to non-secure client devices 54 and 56 is blocked at guard 22C. However, this absolute block may break TCP network protocols and other protocols that require small ACK or acknowledgment packets to flow back to data producing device 54 and UAV 56. In another instance, guard 22C may utilize dynamic filtering options for one-way packet filtering with ACKs going back to the sender (e.g., data producing device 54 and UAV 56). In this instance, guard 22C may be involved with more processing and may have more dynamic capabilities. In the example of FIG. 3, guard 22C may be configured to monitor and control the outgoing traffic to non-secure client devices 54 and 56 universally, needing only the single guard 22C to monitor and control the outgoing traffic regardless of the connection type or the device type of the ultimate non-secure client device 54 and 56.

Contrast this with the "bump-in-the-wire" approach. In this option, guard 22C would be implemented as a respective intermediary on each of the connections between non-secured client devices 54 and 56 and guard 10 to allow traffic to flow in only one direction (i.e., from the non-secure client devices 54 and 56 to guard device 10). Each of the guards would need to be configured independently, as there may not be a common interface for network devices 58A and 58B. Further, a separate guard would be needed for each and every potential connection with a non-secure client device, further increasing the complexity and variability of the overall system.

Another contrasting example to the example of FIG. 3 is to install a separate device (i.e., a cross-domain guard) inline between non-secure client devices 54 and 56 and guard 10. The cross-domain guard may apply the one-way filtering techniques of allowing TCP ACK packets to flow from guard 10 to data producing device 54 and UAV 56 to provide the packet filtering for one-way communication with limited acknowledgement capability. However, each non-secure client device 54 and 56 would still need a respective cross-domain guard device, and each cross-domain guard device may have to be configured independently. Further, a separate cross-domain guard would be needed for each and every potential connection with a non-secure client device, further increasing the complexity and variability of the overall system.

Figure 4:
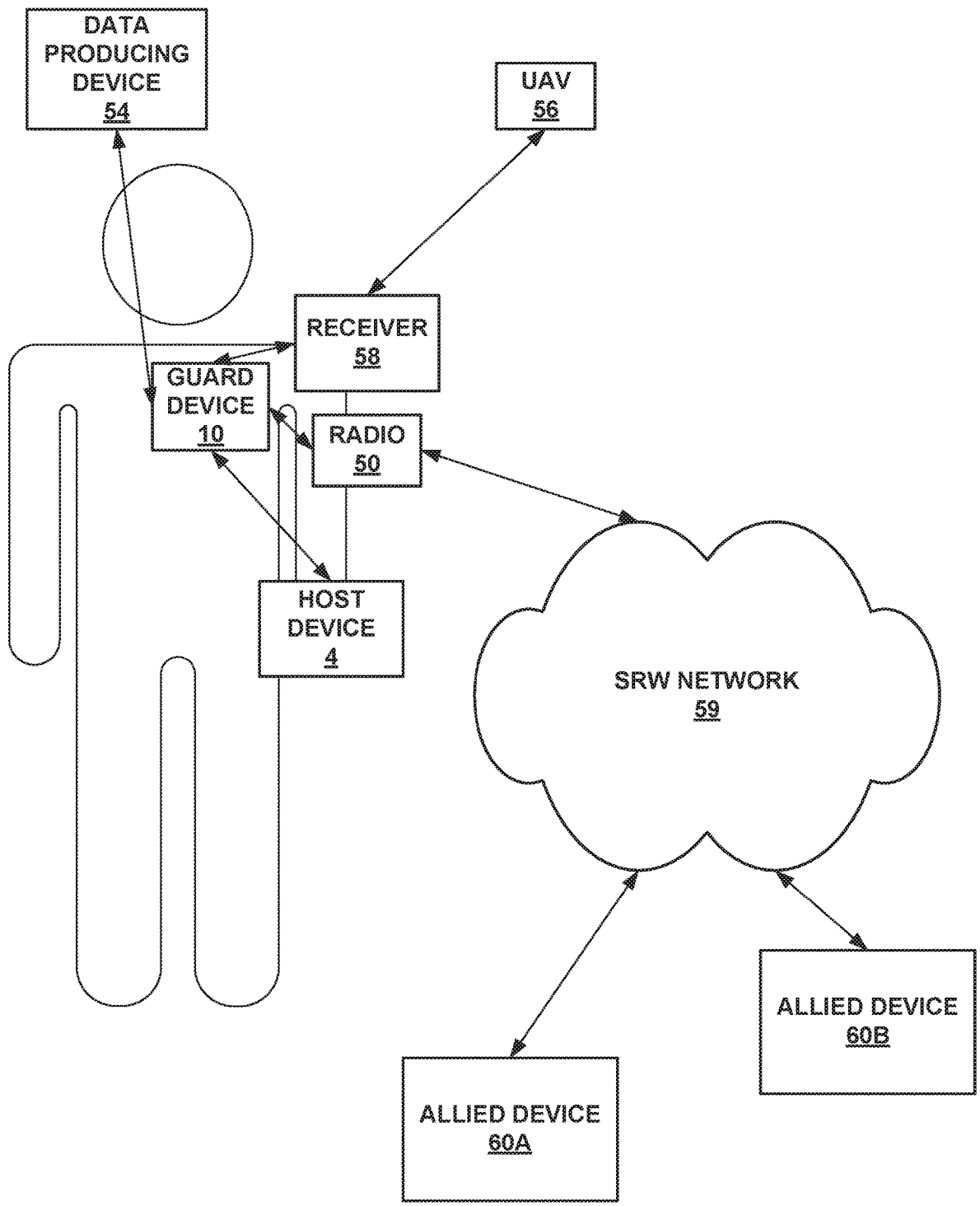
FIG. 4 is a block diagram illustrating an example system that includes a wearable guard device, in accordance with one or more aspects of this disclosure.

FIG. 4 is a block diagram illustrating an example system that includes a wearable guard device 10, in accordance with one or more aspects of this disclosure. The techniques of FIG. 4 may be performed by one or more processors of a computing device, such as guard 10 illustrated in FIG. 1 and/or FIG. 2. For purposes of illustration only, the techniques of FIG. 4 are described within the context of guard 10 of FIG. 1, although computing devices having configurations different than that of guard 10 may perform the techniques of FIG. 4.

In the example of FIG. 4, guard 10 may be connected to non-secured data producing device 54 and receiver 58, which receives information from non-secured UAV 56. Guard 10 is further connected to secured radio 50, which receives communications from allied devices 60A and 60B over a radio network (such as secure radio network 59), which may be a secured network. Since guard 10 is a wearable device, guard 10 may be used by soldiers in the field. Rather than only connecting a single device to host device 4 at any given time, guard 10 may enable multiple devices, both secured and non-secured, to connect to host 4 simultaneously, greatly increasing the efficiency of various operations that the soldier in the field may be tasked with performing.

Figure 5:
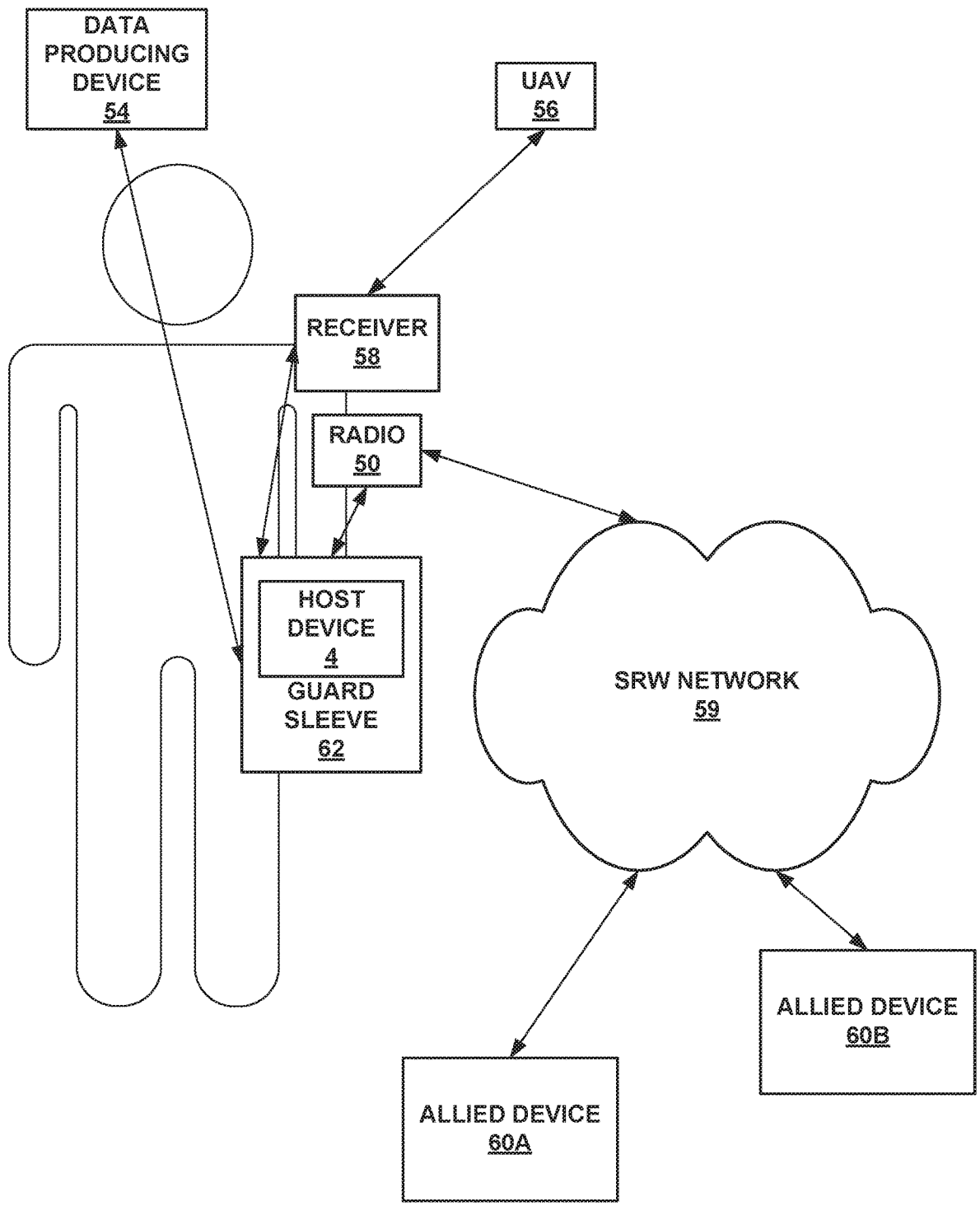
FIG. 5 is a block diagram illustrating an example system that includes a wearable guard device in the form of a sleeve around the host device, in accordance with one or more aspects of this disclosure.

FIG. 5 is a block diagram illustrating an example system that includes a wearable guard device in the form of guard sleeve 62 around host device 4, in accordance with one or more aspects of this disclosure. The techniques of FIG. 5 may be performed by guard sleeve 62, which may have similar functionalities to guard 10 illustrated in FIG. 1 and/or FIG. 2.

Guard sleeve 62 may generally include any mechanism for attaching a guard device, such as guard 10, to the body, clothing, or uniform of a user, or to host 4 itself. Guard sleeve 62 may also include an external CPU that may connect to host 4 rather than guard 10, which is a separate device. However, guard sleeve 62 may still perform the same functions of guard 10, including connecting to multiple devices, both secured and non-secured, and perform particular guard processes on the received non-secured data packets, in accordance with the techniques described throughout this disclosure.

In the example of FIG. 5, guard sleeve 62 may be connected to non-secured data producing device 54 and receiver 58, which receives information from non-secured UAV 56. Guard sleeve 62 is further connected to secured radio 50, which receives communications from allied devices 60A and 60B over secure radio network 59, which may be a secured network. Since guard sleeve 62 is a wearable device that is attached to host 4, guard sleeve 62 may be used by soldiers in the field. Rather than only connecting a single device to host 4 at any given time, guard sleeve 62 may enable multiple devices, both secured and non-secured, to connect to host 4 simultaneously, greatly increasing the efficiency of various operations that the soldier in the field may be tasked with performing.

Figure 6:
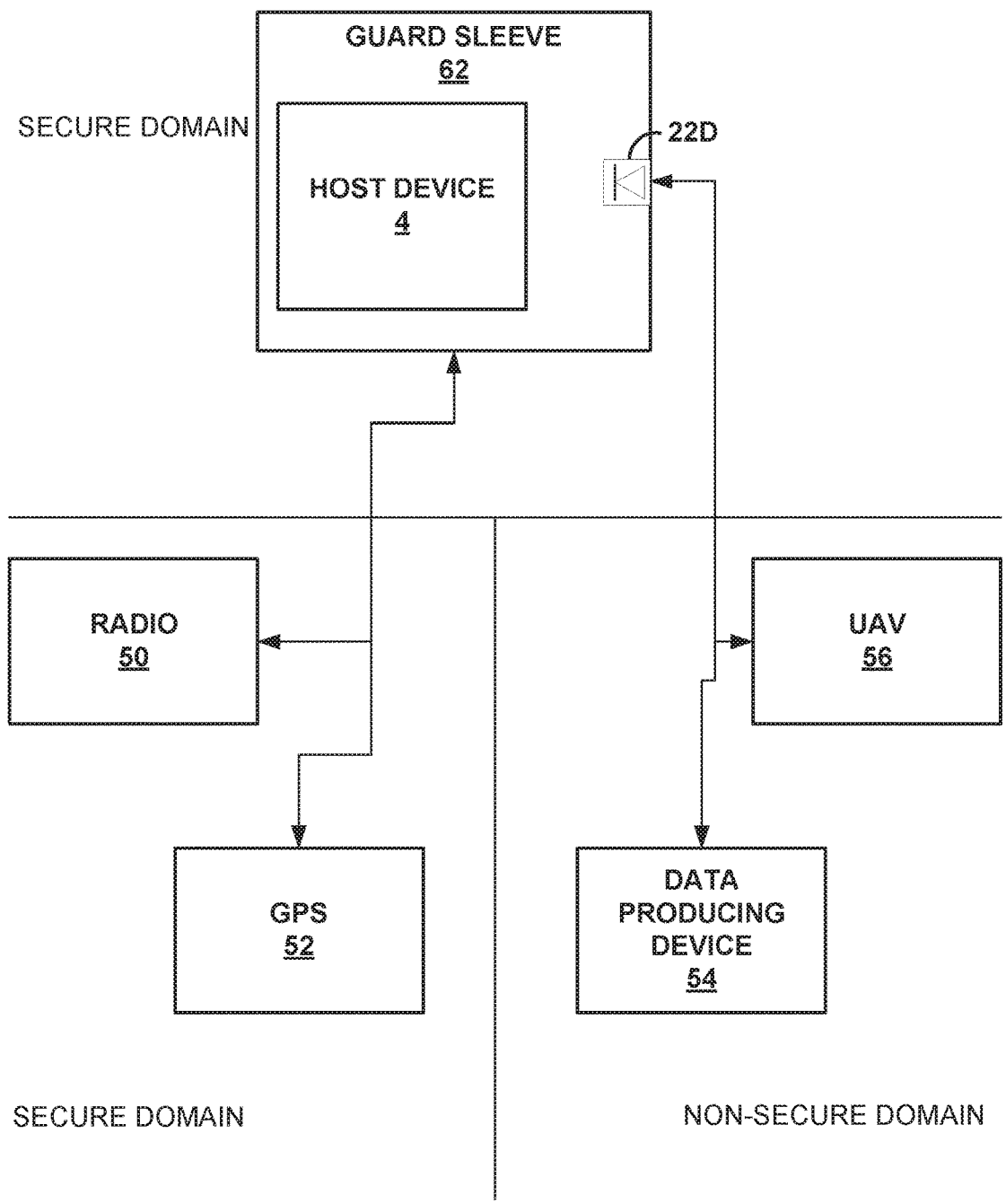
FIG. 6 is a block diagram illustrating an example system that includes a guard device in the form of a sleeve around the host device, in accordance with one or more aspects of this disclosure.

FIG. 6 is a block diagram illustrating an example system that includes guard sleeve 62 configured to receive data packets from secure client devices 50 and 52 and forward the received data packets to a host device 4. Guard sleeve 62, which is attached to host device 4, is further configured to receive data packets from non-secure client devices 54 and 56 and control outgoing communications to the non-secure client devices 54 and 56, in accordance with one or more aspects of this disclosure. The techniques of FIG. 6 may be performed by one or more processors of a computing device, such as guard 10 illustrated in FIG. 1 and/or FIG. 2. For purposes of illustration only, the techniques of FIG. 6 are described within the context of guard 10 of FIG. 1, although computing devices having configurations different than that of guard 10 may perform the techniques of FIG. 6.

In another example, the guard functionalities may be implemented in an advanced CPU within guard sleeve 62 operably connected to host device 4. In such an example, guard sleeve 62 may add more ports to host device 4 and may enable host device 4 to have a fully capable dual stack. As such, the functionality of guard device 10 may be split between guard device 10 and guard sleeve 62. Guard device 10 may process all data packets coming from devices 50 and 52 in the secure domain, and guard sleeve 62 may process all data packets coming from devices 54 and 56 in the non-secure domain.

Figure 7:
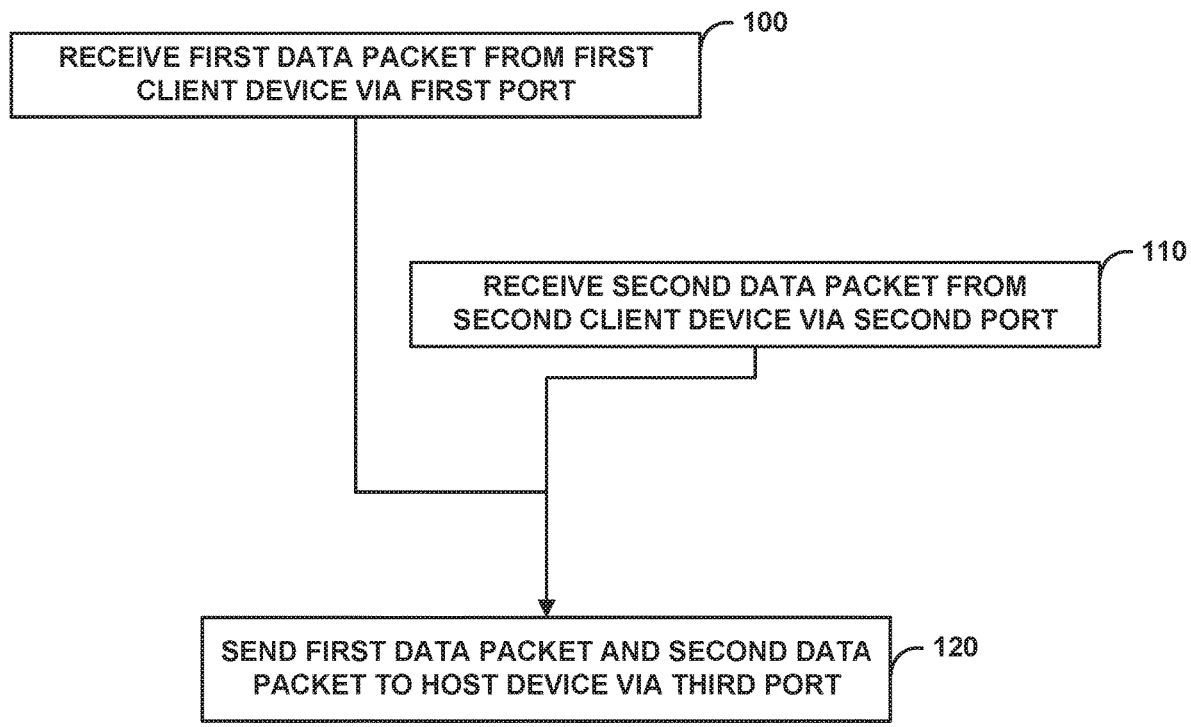
FIG. 7 is a flow diagram illustrating example operations of a guard device that implements data processing techniques in accordance with one or more aspects of this disclosure.

FIG. 7 is a flow diagram illustrating example operations of a guard device that implements data processing techniques in accordance with one or more aspects of this disclosure. The techniques of FIG. 7 may be performed by one or more processors of a computing device, such as guard 10 illustrated in FIG. 1 and/or FIG. 2. For purposes of illustration only, the techniques of FIG. 7 are described within the context of guard 10 of FIG. 1, although computing devices having configurations different than that of guard 10 may perform the techniques of FIG. 7. While the techniques described below with respect to FIG. 7 are described as being performed by processors 14, processors 14 may utilize other modules or applications, such as a virtual machine, to perform all or a portion of the techniques described herein, so as to maintain integrity between the secured data packets and the non-secured data packets.

In accordance with the techniques of this disclosure, processors 14 of guard 10 may receive, via port 12A, a first data packet from non-secure client device 8A (100). Processors 14 of guard 10 may also receive, via port 12B, a second data packet from secure client device 6A (110).

In some examples, based on the sender of the respective data packet, processor 14 may perform separate guard processes on the respective data packet. For instance, processors 14 may execute a separate virtual machine in guard 10, with the virtual machine performing a first guard process on the first data packet based on the security classification of non-secure client device 8A (i.e., non-secure or untrusted) and a second virtual machine performing a second guard process on the second data packet based on the security classification of secure client device 6A (e.g., a secure security classification, such as secret, top secret, classified, or protected). For the second guard process, in some instances, processors 14 may simply forward the second data packet to host 4 via port 12C. In other instances, for the second guard process, processors 14 may analyze contents of the second data packet to determine an identity of the sender of the second data packet or the type of contents in the second data packet prior to forwarding the second data packet to host 4 via port 12C. As the second data packet may come from a secure and trusted client device, processors 14 may refrain from determining an integrity of the received data and performing a virus scan operation on the second data packet.

For the first guard process, processors 14 of guard 10 may utilize the separate virtual machine to determine an integrity of the first data packet based at least in part on a type of connection between guard 10 and non-secure client device 8A and a data type of the first data packet. In other words, the data packet may have a different structure depending on the type of data stored within the data packet and the protocol used to transmit the data packet to guard 10. As such, the specific method for determining the integrity of the first data packet may vary based on the expected structure of the first data packet. If the virtual machine determines that the integrity of the first data packet is above a threshold integrity level, processors 14 may send the first data packet to host 4 via port 12C.

Part of the integrity check may include processors 14 utilizing the separate virtual machine to determine that the actual structure of the first data packet matches an expected structure based on the type of data stored within the data packet and the protocol used to transmit the data packet to guard 10. For instance, if non-secure client device 8A sends an image file over a USB connection, guard 10 may expect the first data packet to have a particular structure with particular bitfields filled out in particular ways. The virtual machine may determine that the first data packet passes the integrity check if the bitfields match the expected structure.

Another part of the integrity check may include processors 14 utilizing the separate virtual machine to perform a virus scan operation on the first data packet. The virus scan operation may include comparing certain values within the data packet to known virus or malware structures. If the virtual machine determines that the first data packet contains a virus or malware, then processors 14 may block the first data packet from reaching host 4. Conversely, if processors 14 determines that the virus scan operation shows no harmful data in the first data packet, processors 14 may forward the first data packet to host 4 via port 12C.

Processors 14 of guard 10 may send, via port 12C, the first data packet and the second data packet to host 4 (120). Port 12C may forward the respective data packets to host 4 either upon receipt of the respective data packets or after the respective data packets have been processed. In other words, port 12C may not necessarily forward the first data packet and the second data packet simultaneously, but instead forward the first data packet and the second data packet after processors 14 determines the respective data packet to be safe to forward to host 4 in the respective data packet's own respective processing loop. The timing with which processors 14 forward the first data packet is independent of the timing with which processors 14 forward the second data packet.

In some examples, processors 14 may simply forward the first data packet and the second data packet to host 4 upon receiving the respective data packets. In other examples, as described above, processors 14 may implement some form of guard process to evaluate the first data packet received from non-secure client device 8A. Upon determining that the first data packet meets a threshold level of integrity, processors 14 may forward the first data packet to host 4 via port 12C. In still other instances, processors 14 may process certain information regarding the second data packet (i.e., sender information or content information) prior to forwarding the second data packet to host 4.

In some examples, processors 14 of guard 10 may receive an outgoing message to be sent to non-secure client device 8A. For instance, host 4 may attempt to send an ACK message to non-secure client device 8A. Prior to forwarding the ACK message, processors 14 of guard 10 may scan the outgoing message to determine whether the outgoing message contains secure information that would be improper for a non-secure client device to receive. In response to determining that the outgoing message does not contain secure information, processors 14 of guard 10 may send the outgoing message to non-secure client device 8A via port 12A. However, in response to determining that the outgoing message contains secure information, processors 14 of guard 10 may refrain from sending the outgoing message to non-secure client device 8A so as to protect the integrity of the secured system.

In some other examples, rather than expecting host 4 to produce and send ACK messages, processors 14 may utilize a proxy module to produce an ACK message. For instance, if the first data packet was part of a TCP message, processors 14 may utilize the proxy module to create an ACK message and send the ACK message to non-secure client device 8A.

In other examples, processors 14 of guard 10 may prevent all outgoing traffic from reaching non-secure client device 8A. In such examples, processors 14 of guard 10 may receive an outgoing message to be sent to non-secure client device 8A. Upon determining that the intended recipient of the outgoing message is a non-secure client device (i.e., non-secure client device 8A), processors 14 of guard 10 may refrain from sending the outgoing message to non-secure client device 8A so as to protect the integrity of the secured system.

Figure 8:
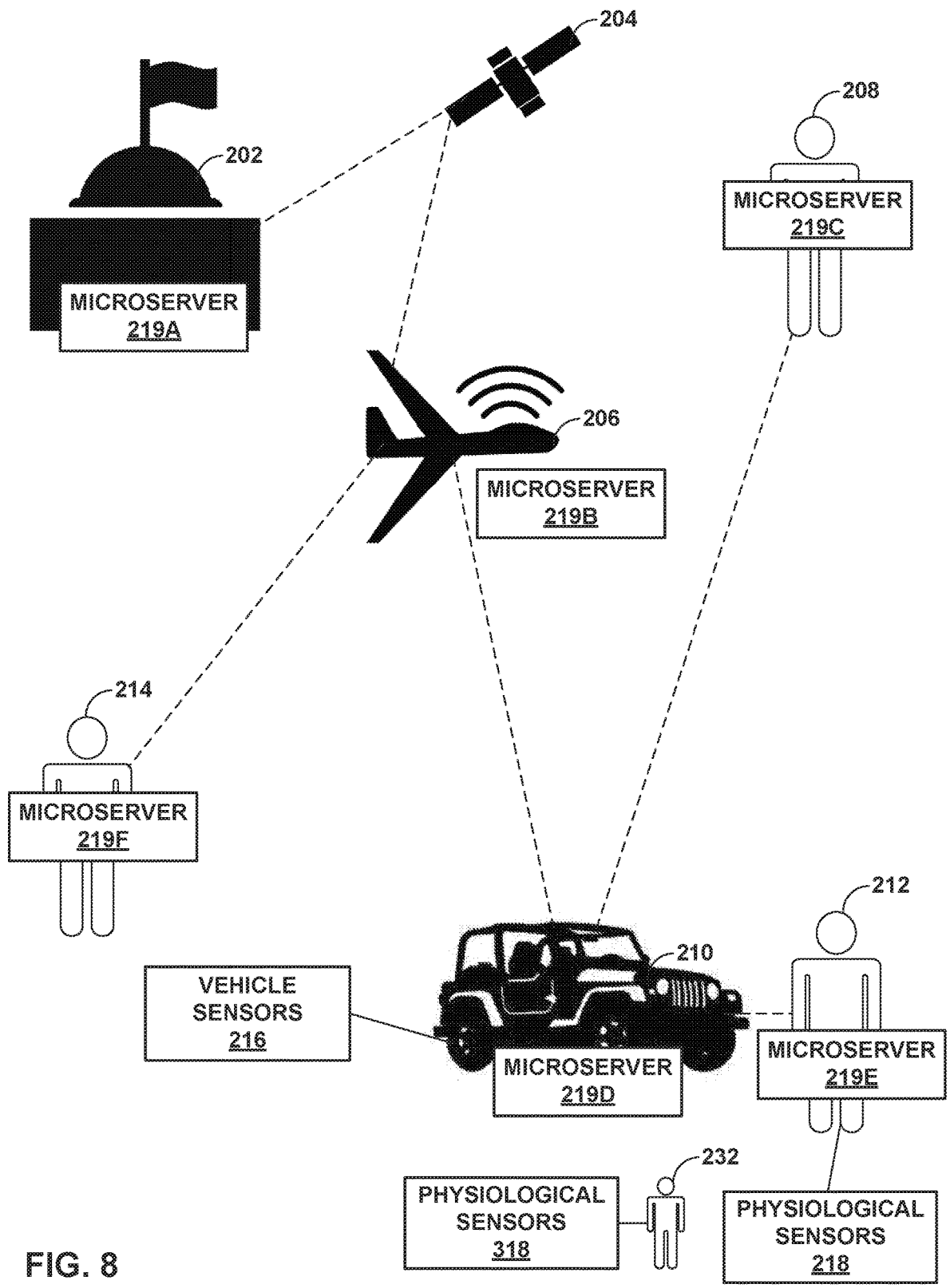
FIG. 8 is a block diagram illustrating an example instrumented tactical network with verification techniques in accordance with one or more aspects of this disclosure.

FIG. 8 is a block diagram illustrating an example instrumented tactical network with verification techniques in accordance with one or more aspects of this disclosure. The tactical network includes headquarters 202, antenna 204, unmanned aerial vehicle (UAV) 206, users 208, 212, and 214, and vehicle 210. User 212 may utilize physiological sensors 218 and vehicle 210 may utilize vehicle sensors 216. Each of entities 202, 206, 208, 210, 212, and 214 may have a respective micro-server 219A-219F (collectively "micro-servers 219") that utilizes the techniques described herein for identification authorization.

A first example of the authentication devices referred to throughout this disclosure are physiological sensors 218. Physiological sensors 218 may be any sensor, attached to or otherwise carried by a user, that may detect something that the respective user has, something that the respective user is, or something that the respective user knows. For instance, physiological sensors 218 may include one or more of a voice recognition sensor, a hand geometry sensor, a hand grip sensor, a fingerprint sensor, an electrocardiogram (ECG) sensor, an ear print sensor, a radio frequency identification tag, a proximity sensor, a password entry device, a radio device, a gait sensor (local and remote), a facial recognition camera, a palm vein pattern sensor (i.e., a sensor specifically configured to measure and determine a pattern in the veins of a user's palm), a global positioning system, a shoe tap input sensor, a finger tap input sensor, or a keystroke analyzer device. Each authentication device may produce one or more of a passcode, signature, profile data, biometric information, or other authentication data that can be stored on a security device.

A second example of the authentication devices referred to throughout this disclosure are vehicle sensors 216. Vehicle sensors 216 may be any sensor, attached to or otherwise utilized by a vehicle, that may send authentication factors to a respective micro-server (e.g., micro-server 219D). Examples of vehicle sensors 216 may include one or more of a radio frequency identification chip, a proximity sensor, a password entry system, a keystroke analyzer, a voice recognition sensor, or a global positioning system, among other things.

In the example of FIG. 8, users 208, 212, and 214 are communicating amongst one another. Each of users 208, 212, and 214 has some kind of radio that interconnects them to other entities (e.g., vehicle 210, UAV 206, etc.) which can forward the communications across different radio networks. Micro-server 219E of user 212 may read data from physiological sensors 218 (e.g., an ECG, voiceprints, and/or other authentication signals) to determine that user 212 is actually user 212. Micro-server 219E may also check with micro-server 219D at vehicle 210 to verify signatures. Micro-server 219C and micro-server 219F may do the same with users 208 and 214, respectively. Micro-server 219E may share its "approval" with micro-server 219C and micro-server 219F in such a way that micro-server 219C and micro-server 219F can trust micro-server 219E. Micro-servers 219, in general, accomplish this by building a sequence of data packets that indicate a message with the "approval" or "disapproval" combined with the multiple print signature data, encrypting the data packets, signing the data packets, and sending the data packets to other instances of micro-servers 219. Micro-servers 219C and 219F receive and decrypt the message, and then run a separate validation of user 212. If the validations all match the identity of user 212, then communications are allowed amongst users 208, 212, and 214. If the validations do not match the identity of user 212, then micro-servers 219C and 219F suspect user 212 or micro-server 219E may be compromised and can recheck and initiate protocols and policies in response (such as dropping communications).

This example shows how the various micro-servers 219 interact to validate users and verify signatures. If at any time the validation fails, then cut-off protocols may kick-in to prevent communications compromises. In some cases, the node (e.g., the device being accessed by one of users 208, 212, or 214) could still participate in data routing. In other cases, the node may be cut-off completely. For example, if a device being accessed by user 212 in FIG. 8 is sensed to be compromised, then any of micro-servers 219 may cut-off all communications with user 212. However, if vehicle 210 is sensed to be compromised, cutting off communication from vehicle 210 prevents user 212 from communicating as well. In this case, any user in vehicle 210 is blocked, but the system may still allow vehicle 210 to forward packets through it, until some other error is detected.

Micro-server 219E may also verify the identity of "remote users" (i.e., users not directly using the client devices. For instance, user 212 may interact with user 232, and user 212 may wish to verify the identity of user 232. Physiological sensors 318, which may be similar to physiological sensors 218, may take various measurements of user 232 and create authentication factors for user 232. Physiological sensors 318 may send the authentication factors to micro-server 219E, which may proceed to perform the authentication process described herein to determine an identity of user 232, including whether user 232 is an allied, or trusted, user.

When micro-server 219E calculates the "trusted" status of both its local user and its remote users, micro-server 219E may apply threshold values to the "trust" values to get different affects. If micro-server 219E determines that the trust level drops below a threshold, micro-server 219E may limit or cut-off communications to the client. Micro-server 219E may use different thresholds for different effects. For example, if micro-server 219E calculates a probability that indicates there is a 90% chance that the user is valid, then micro-server 219E may enable all communications. However, if the probability drops between 80% and 89% that the user is valid, then any human voice interaction may be cut-off, or micro-server 219E may drop a chat window or automated system data that displays information on a screen such that no passive listener or active talker can participate, but automated systems without displays and data relay/routing participation will still work. If the probability drops to 70% to 79%, then micro-server 219E may block automated systems with no display, but still allow such systems to participate in data relay/routing to help the rest of the airborne network if needed (e.g., the system may passively listen to packets and route the data packets, which may be crucial to coalition devices). Further, if the probability drops below 69%, all communications may be cut-off to prevent even routing participation. While these levels are one example of the probability thresholds, these levels may be configurable and may also be set based on threat level.

Figure 9A:
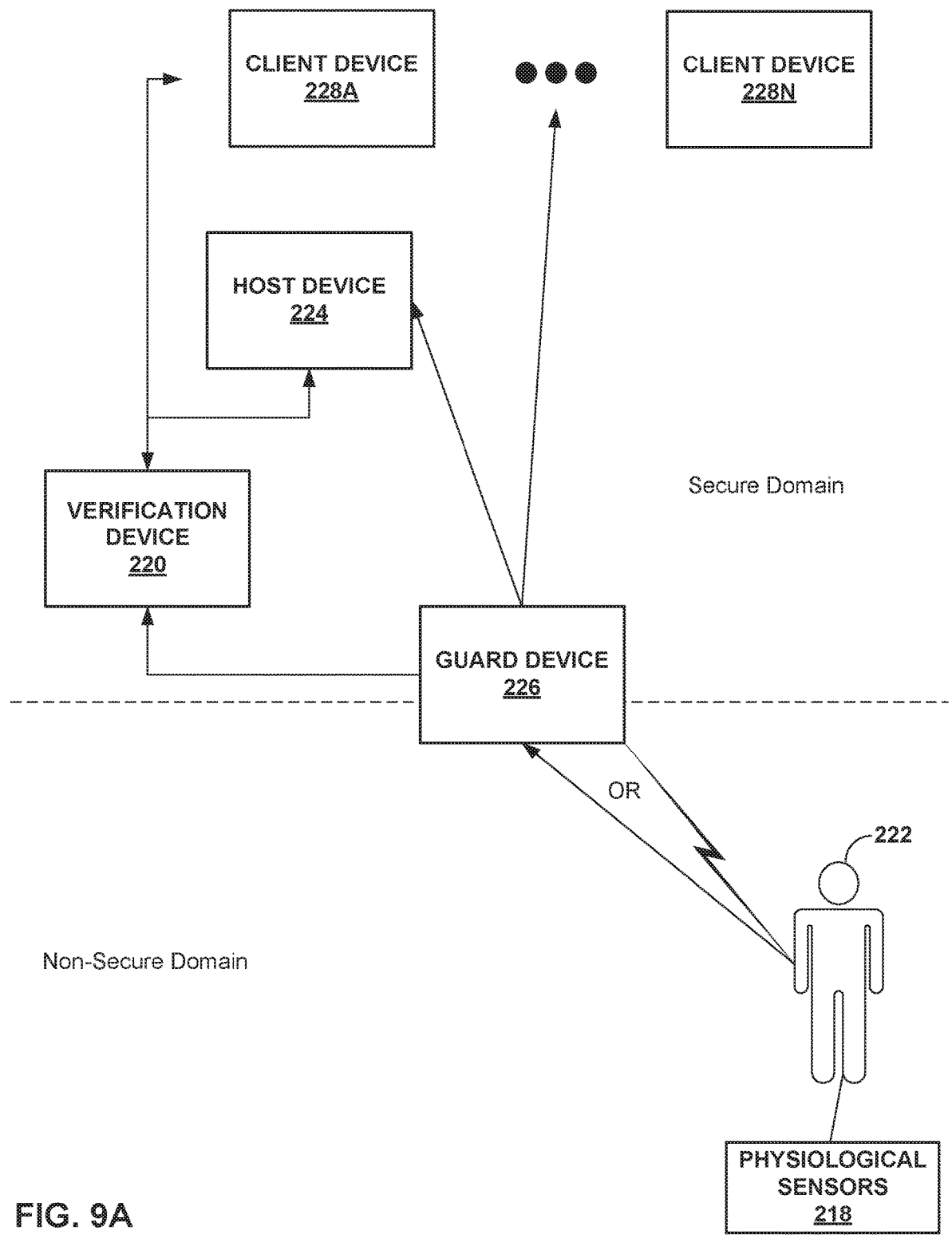
FIGS. 9A-9C is a block diagram illustrating an example authentication architecture in accordance with one or more aspects of this disclosure.
Figure 9B:
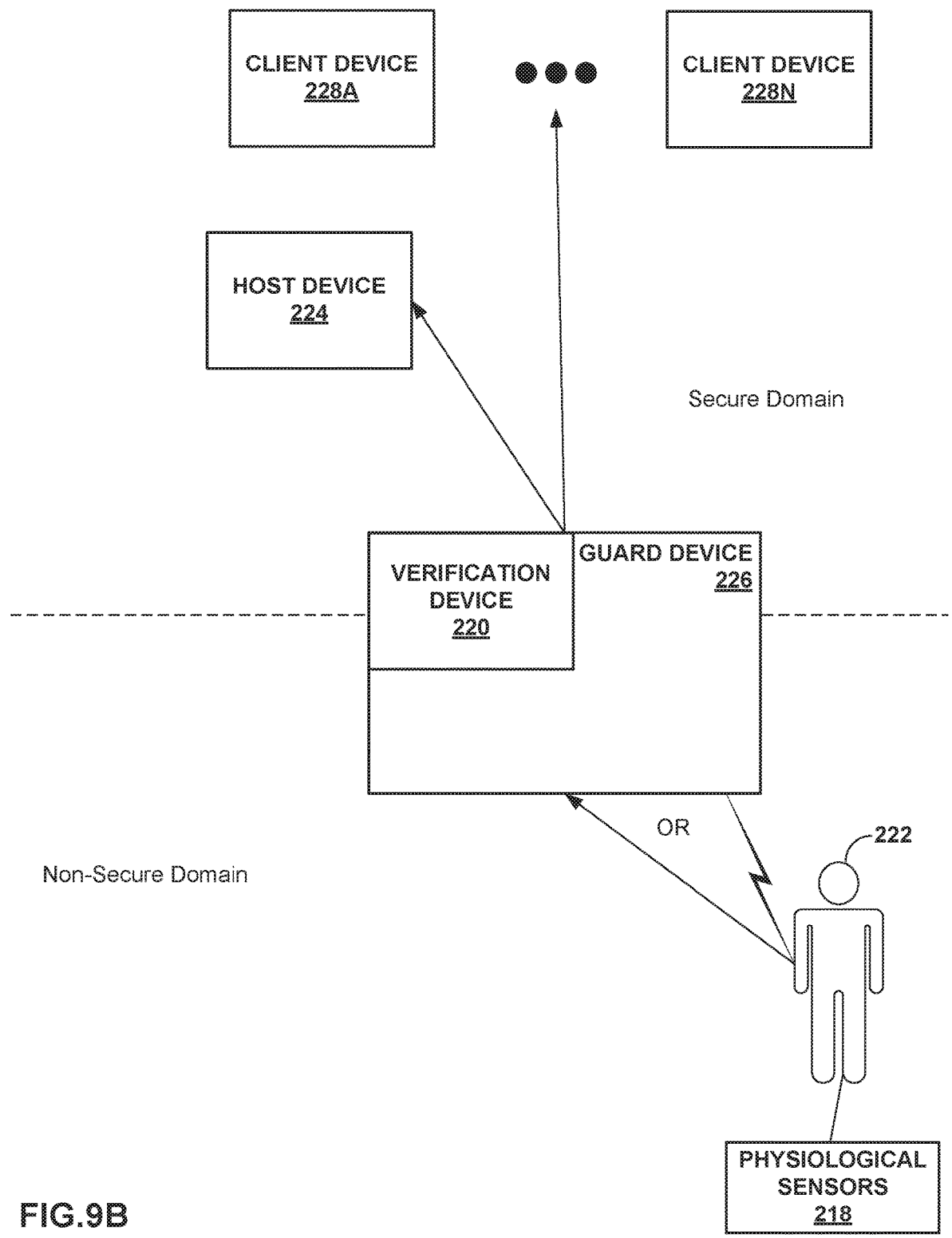
Figure 9C:
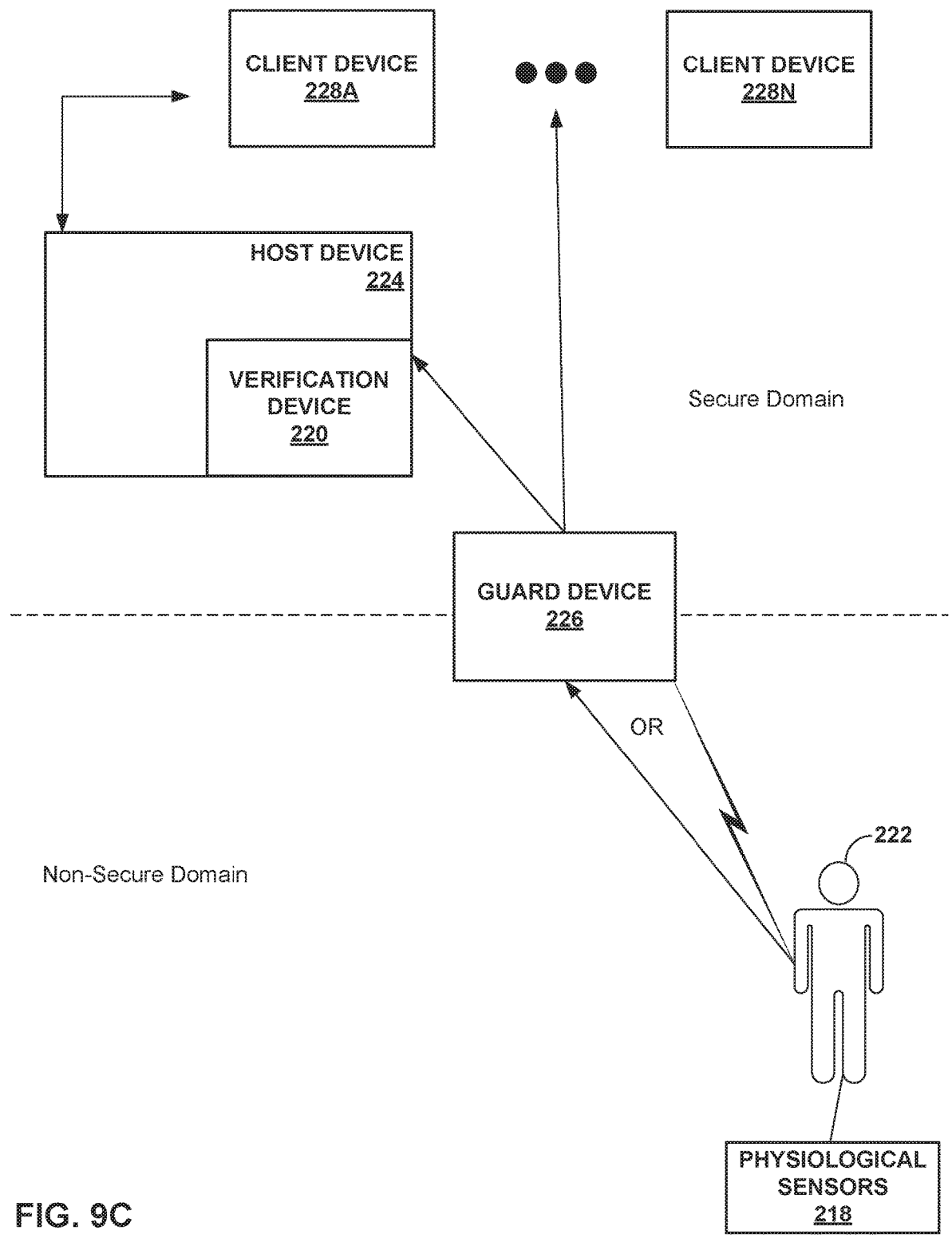

FIGS. 9A-9C are block diagrams illustrating example authentication architectures in accordance with one or more aspects of this disclosure. In the example of FIGS. 9A-9C, physiological sensors 218, similar to physiological sensors 218 described above with respect to FIG. 8, may receive input from user 222 to determine a respective authentication factor for user 222 (e.g., a passcode, a signature, profile data, authentication data stored on a security device, or biometric information). Verification device 220, which may be a micro-server (e.g., microserver 219) or some other device configured to perform the authentication techniques described herein, may receive an authentication factor from each sensor of physiological sensors 218 and determine whether user 222 is a particular trusted user of the devices in the tactical network. Verification device 220 may send the results of the authentication process (i.e., a set of one or more data packets with either an authorization message or a denial message) to host device 224 (which may be similar to host device 4 of FIG. 1) or any of client device 228A-228N. Verification device 220, host device 224, or guard device 226, based on the results of the authentication process, may either grant or deny user 222 access to host device 224 and/or client devices 228A-228N.

Each of FIGS. 9A-9C show different arrangements or implementations of verification device 220 in the authentication system described herein. In the example of FIG. 9A, verification device 220 may be a separate, stand-alone device, such as a micro-server device. In such examples, physiological sensors 218 may send the various authentication factors to guard device 226, which, after ensuring the safety and integrity of the data, forwards the authentication factors to verification device 220. Verification device 220 may perform the authentication process described herein, and upon verifying the identity of user 222, send an authentication confirmation to any of host device 224 and/or client devices 228A-228N.

In the example of FIG. 9B, verification device 220 may be a hardware or software component embedded in guard device 226. In such examples, physiological sensors 218 may send the various authentication factors to guard device 226, which, after ensuring the safety and integrity of the data, uses the functionality of verification device 220 to perform the authentication process described herein. Upon verifying the identity of user 222, guard device 226 may send an authentication confirmation to any of host device 224 and/or client devices 228A-228N.

In the example of FIG. 9B, verification device 220 may moderate the communication between physiological sensors 218, which are in a non-secure domain (or a "low" side), and host device 224, which is in a secure domain (or a "high" side). The high side of verification device 220 (e.g., the portion of verification device 220 in communication with devices in the secure domain) may implement a Commercial Solutions for Classified (CSfC) server, or any other security protocol, and a one-way guard between the high and low sides. The low side (e.g., the portion of verification device 220 in communication with physiological sensors 218 in the non-secure domain), may collect data and interact with physiological sensors 218 of user 222, only sharing data one-way through the guard to the high side of verification device 220 for use by host device 224. In this version of the techniques, physiological sensors 218 may be wired directly to verification device 220, but would allow for host device 224 to wirelessly connect to verification device 220, as verification device has the high side communication capabilities.

In other examples, verification device 220 is entirely in the non-secure domain, forwarding only the authentication confirmation to guard device 226 for analysis. As such, verification device 220 may not be limited in the way that verification device 220 communicates with physiological sensors (e.g., verification device 220 may be wired to physiological sensors 218 or wirelessly connected to physiological sensors 218, such as using Bluetooth or Wi-Fi connections).

In the example of FIG. 9C, verification device 220 may be a hardware or software component embedded in host device 225. In such examples, physiological sensors 218 may send the various authentication factors to guard device 226, which, after ensuring the safety and integrity of the data, forwards the authentication factors to host device 224. Host device 224 may use the functionality of verification device 220 to perform the authentication process described herein. Upon verifying the identity of user 222, host device 224 may send an authentication confirmation to any of client devices 228A-228N, or enable user access to host device 224 itself.

Figure 10:
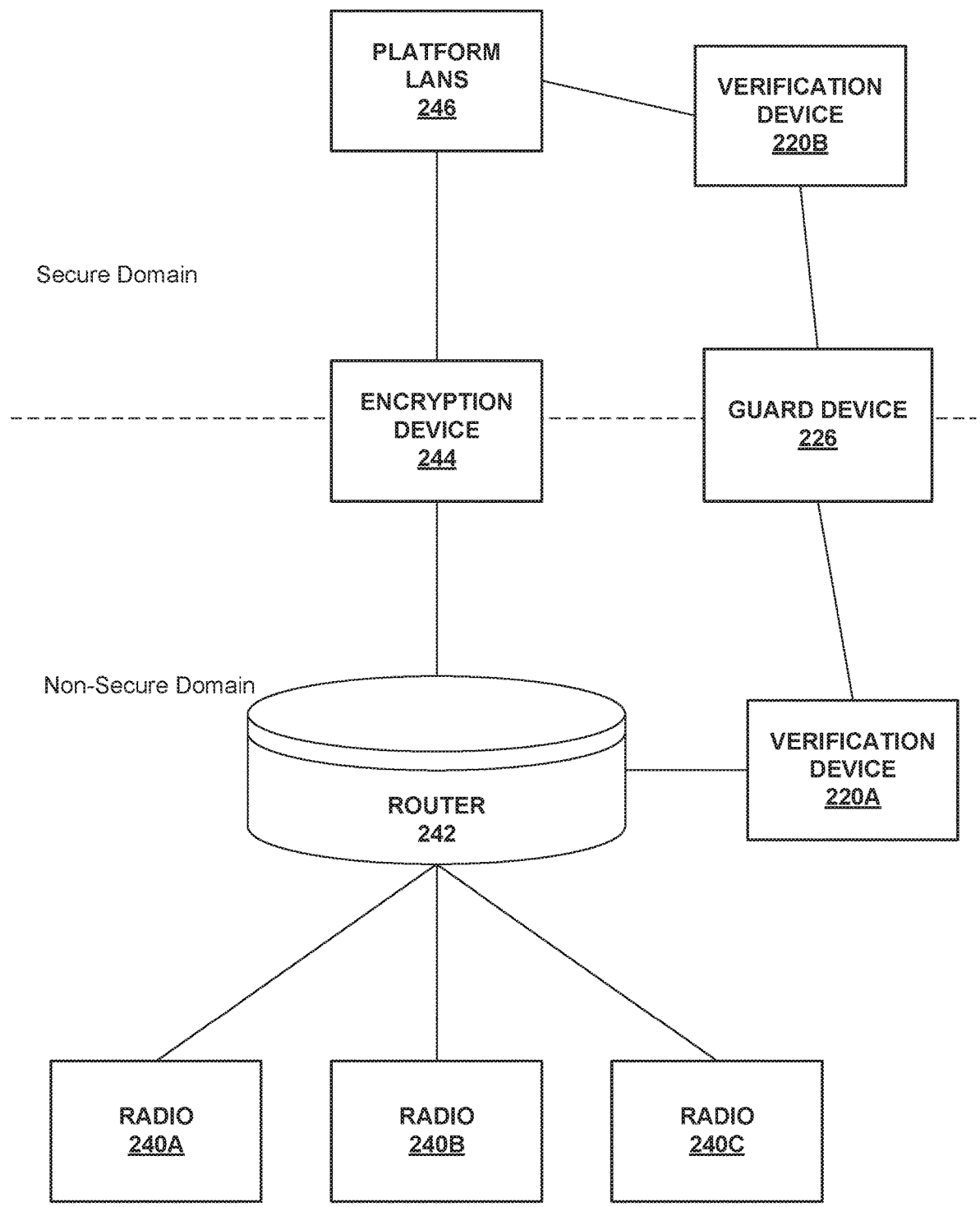
FIG. 10 is a block diagram illustrating an example router-based integration of an authentication architecture in accordance with one or more aspects of this disclosure.

FIG. 10 is a block diagram illustrating an example router-based integration of an authentication architecture in accordance with one or more aspects of this disclosure. In this example, low-side verification device 220A, which receives authentication factors from various authentication devices in non-secure domains, is connected to (or embedded within) router 242. In examples where router 242 transmits general, non-authentication data (e.g., data other than authentication messages) to other devices, router 242 may transmit the data via any of wireless radios 240A-240C (collectively, "wireless radios 240") or over platform local area networks (LANs) 246. In other examples, where router 242 transmits data received via wireless radios 240 to platform LANs 246 in a secure domain, router 242 may send the data to encryption device 244 over a secure wired connection, which forwards the data through the platform LANs 246, which may further transmit the data to other devices. Router 242 may generally transmit data either through a wired connection or a wireless connection.

In some examples, router 242 may be part of an airborne network built for the convergence of many types of wireless radios 240 used across many aerial and ground radio systems in tactical networks to form a dynamic ad hoc multi-radio fault tolerant network using a diverse mix of radios and waveforms. Some protocols that router 242 may process include AN/PRC-154, AN/PRC-152A, AN/PRC-117G, SRW, ANW2, QNT, TTNT, LTE, SatCom, Wi-Fi, etc. Verification devices 220A and 220B may include an authentication system to verify the participants within the network before an endpoint can join and communicate.

In another example, router 242 may receive authentication factors and/or authentication messages from authentication devices in the non-secure domain via wireless radios 240. Router 242 may pass these authentication factors to low-side verification device 220A, which, as described above, is a standalone device or a software or hardware component embedded in router 242.

Low-side verification device 220A may collect raw data from authentication devices on the "low-side" (i.e., the non-secure domain) received via router 242 or directly from authentication devices in the non-secure domain. Low-side verification device 220A may reformat or package the collected raw data such that it is in condition to be sent across guard device 226 and into the "high-side" (i.e., the secure domain). Guard device 226 may then forward the received data to high-side verification device 220B, which may be configured to perform the authentication techniques described herein. High-side verification device 220B may further receive additional authentication factors from authentication devices in the secure domain.

If high-side verification device 220B determines that the result of the verification process is that the user is not a trusted user, high-side verification device 220B may send a failure indication through guard device 226 to low-side verification device 220A. Low-side verification device 220A may configure router 242 to cut off communication with the devices that the failed user was attempting to access as described above with respect to FIG. 8, ensuring safety in the system.

Figure 11:
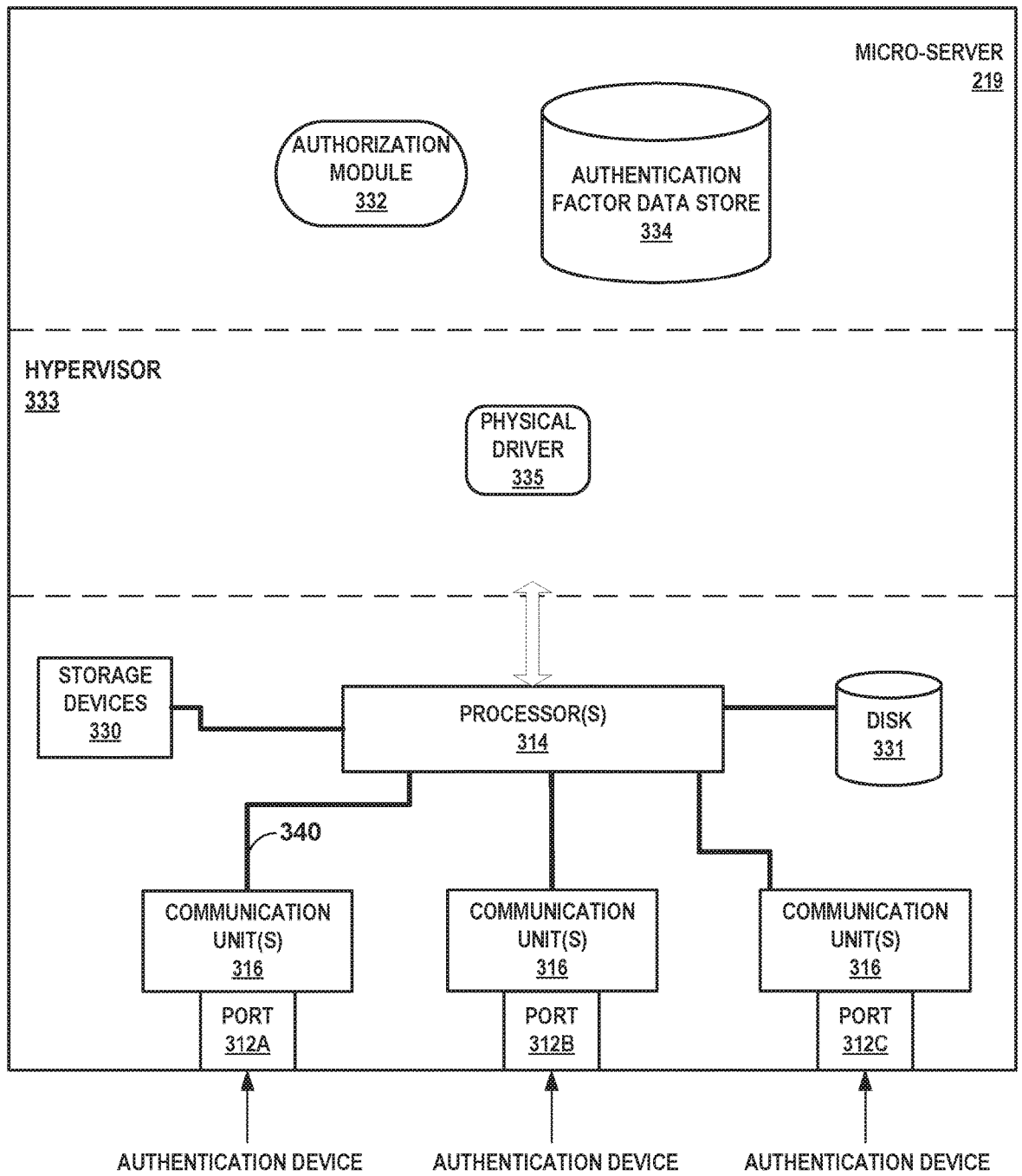
FIG. 11 is a block diagram illustrating an example micro-server device of FIG. 8 in more detail.

FIG. 11 is a block diagram illustrating a detailed example of micro-server 219 configured to receive authorization factors from authentication devices and to analyze the authentication factors to determine the identity of a potential user of a client device, in accordance with one or more techniques of this disclosure. FIG. 11 illustrates some particular examples of micro-server 219, and many other examples of micro-server 219 may be used in other instances and may include a subset of the components included in example micro-server 219 or may include additional components not shown in FIG. 11.

For example, micro-server 219 may include a battery to provide power to the components of micro-server 219, or micro-server 219 may include more ports than three (e.g., four or more ports). Micro-server 219 may also be integrated with a cross-domain guard and/or a hub and include the components shown in FIG. 2, or may be integrated with the client device itself. Similarly, the components of micro-server 219 shown in FIG. 2 may not be necessary in every example of micro-server 219. For example, in some configurations, micro-server 219 may not include authorization module 332 and may instead include a virtual machine that performs the same functions as authorization module 332. As shown in the example of FIG. 11, micro-server 219 includes one or more processors 314, one or more communication units 316, authorization module 332 executable by one or more processors 314, and one or more storage devices 330.

One or more storage devices 330 of micro-server 219 include authorization module 332 and authentication factor data store 334. One or more storage devices 330 may be configured to store information within micro-server 219 during operation. Storage device 330, in some examples, is described as a computer-readable storage medium. In some examples, storage device 330 is a temporary memory, meaning that a primary purpose of storage device 330 is not long-term storage. Storage device 330, in some examples, are described as volatile memories, meaning that storage device 330 does not maintain stored contents when the computing device is turned off. Examples of volatile memories include RAM, DRAM, SRAM, and other forms of volatile memories known in the art. In some examples, storage device 330 is used to store program instructions for execution by processors 314.

Storage devices 330, in some examples, also include one or more computer-readable storage media. Storage devices 330 may be configured to store larger amounts of information than volatile memory. Storage devices 330 may further be configured for long-term storage of information. In some examples, storage devices 330 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Disk 331 represents computer readable storage media that includes volatile and/or non-volatile, removable and/or non-removable media implemented in any method or technology for storage of information such as processor-readable instructions, data structures, program modules, or other data. Computer readable storage media includes, but is not limited to, random access memory (RAM), read-only memory (ROM), EEPROM, flash memory, CD-ROM, digital versatile discs (DVD) or other optical storage, magnetic cassettes, magnetic tape, magnetic disk storage or other magnetic storage devices, or any other medium that can be used to store the desired information and that can be accessed by processor 314.

Communication channels 340, represented by the solid lines in FIG. 11, may interconnect each of (or some sub-combination of) the components 314, 316, 312A, 312B, 312C, and 330 for inter-component communications (physically, communicatively, and/or operatively). In some examples, communication channels 340 may include a system bus, a network connection, an inter-process communication data structure, or any other method for communicating data. The communication channels for a particular set of components may be isolated from another set of components.

One or more communication units 316 of micro-server 219 may communicate with external devices, such as a server device, a client device, secure client devices, and/or non-secure client devices, via one or more wired and/or wireless networks by transmitting and/or receiving network signals on the one or more networks. Communication units 316 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, micro-server 219 utilizes communication units 316 to wirelessly communicate with another computing device that is operably coupled to micro-server 219, such as physiological sensors 218 of FIG. 8.

In some examples, communication units 316 may include a sufficient number of communication units such that each of ports 312A-312C connects to components in micro-server 219 through a respective communication unit. In other words, port 312A may utilize a first one of communication units 316 to receive data packets from an outside computing device and to send the received data packets to the correct units for processing. In other examples, the respective ports 312A-312C may be configured to automatically send the received packets to the correct units on its own. In other words, communications channels for different sets of components can be isolated.

One or more processors 314, in one example, are configured to implement functionality and/or process instructions for execution within micro-server 219. For example, processors 314 may be capable of processing instructions stored in storage device 330. Examples of processors 314 may include, any one or more of a microprocessor, a controller, a digital signal processor (DSP), an application specific integrated circuit (ASIC), a field-programmable gate array (FPGA), or equivalent discrete or integrated logic circuitry.

In instances where authentication module 332 is a virtual machine, micro-server 219 executes a hypervisor 333 to manage the virtual machines. Example hypervisors include Kernel-based Virtual Machine (KVM) for the Linux kernel, Xen, ESXi available from VMware, Windows Hyper-V available from Microsoft, and other open-source and proprietary hypervisors. Hypervisor 333 may represent a virtual machine manager (VMM). Hypervisor 333 includes a physical driver 335 to use the physical function provided by a network interface card. In other examples where authentication module 332 is not a virtual machine, micro-server 219 may not include hypervisor 333.

Micro-server 219 may include authorization module 332. Module 332 may perform operations described using software, hardware, firmware, or a mixture of hardware, software, and firmware residing in and/or executing at micro-server 219. Micro-server 219 may execute module 332 with one or more processors. Micro-server 219 may execute module 332 as a virtual machine executing on underlying hardware. Module 332 may execute as a service or component of an operating system or computing platform. Module 332 may execute as one or more executable programs at an application layer of a computing platform. Module 332 may be otherwise arranged remotely to and remotely accessible to micro-server 219, for instance, as one or more network services operating at a network in a network cloud. In other words, module 332 may not be executing at micro-server 219. Instead, module 332 may be executing at a remote computing system (e.g., a server).

Authorization module 332 may be stored in long-term storage, such as storage 30. However, when authorization module 332 are executed by processor 14, processor 14 may read authorization module 332 into volatile memory, such as disk 31. Authorization module 332 may be stored in disk 31 throughout processor 14's execution of authorization module 332.

In accordance with the techniques of this disclosure, authorization module 332 may receive, in a secure domain, an authentication factor from at least three authentication devices of a group of three or more authentication devices (e.g., physiological sensors 218). At least one authentication device in the group of three or more authentication devices is in a non-secure domain. Further, each respective authentication factor comprises a respective identifier of a respective user of the respective authentication device. For instance, authorization module 332 may receive a password from a password input system, a vocal pattern from a voice recognition sensor, and a fingerprint scan from a fingerprint sensor.

Authorization module 332 may determine a probability that the respective user of each respective authentication device is a particular trusted user based on the received authentication factors. For instance, authorization module 332 may determine that the received password may match a stored password for the particular trusted user in authentication factor data store 334. Further, authorization module 332 may determine that the vocal pattern may be an 80% match to a stored vocal pattern for the particular trusted user in authentication factor data store 334. Finally, authorization module 332 may determine that the fingerprint scan is a match with a stored fingerprint scan for the particular trusted user in authentication factor data store 334. Based on this combination of determinations, authorization module 332 may determine a probability that the user that provided each of these authentication factors is the particular trusted user, such as by averaging the percentages of the matches, taking a maximum percentage, taking a minimum percentage, taking each percentage separately, or combining the percentages of the matches in some other means.

In some examples, authorization module 332 may add quality weights to each authentication probability and combine each of the probability values to determine an overall probability. These quality weights may include both the quality of the measurement and the reliability of the particular authentication factor. For instance, if a particular authentication factor is generally more reliable in identifying a user or the measurement taken was of a high quality, authorization module 332 may set the quality weight to a higher value. Alternatively, if the particular authentication factor is generally less reliable in identifying a user or the measurement taken was of a low quality, authorization module 332 may set the quality weight to a lower value. In some examples, if the specific authentication data is below a minimum quality, authorization module may set the overall value for that authentication factor to 1. Alternatively, if the identity of the user does not match the particular trusted user, authorization module may set the overall value for that authentication factor to 0 and report a false attempt to the client device.

Authorization module 332 may compare the probability to a threshold authentication probability. In this comparison, authorization module 332 may determine whether the probability exceeds the threshold authentication probability. For instance, authorization module 332 may only send an authorization to the client device if authorization module 332 determines with 95% confidence that the user is the particular trusted user. In other instances, authorization module 332 may use other thresholds, or may use stepped thresholds to provide more access upon higher probability determinations. Responsive to determining that the probability exceeds the threshold authentication probability, authorization module 332 may send an authentication confirmation to the client device (e.g., host 4 of FIG. 1), thereby enabling access to one or more applications on the client device. In some instances, in addition to performing the authentication locally, authorization module 332 may also send the received authentication factors to a remote server for additional confirmation and only enable access to the applications on the client device once the additional confirmation is received from the remote server.

Conversely, responsive to determining that the probability does not exceed the threshold authentication probability, in some instances, authorization module 332 may send an indication to the remote server device that an untrusted user attempted to gain access to the client device to disable a login credential for the particular user. In other instances, responsive to determining that the probability does not exceed the threshold authentication probability, authorization module 332 may attempt to send the authentication factors and a request to verify the identity of the respective user of the respective authentication device to a remote server and receive one of the identity of the respective user of the respective authentication device or an indication that an untrusted user attempted to gain access to the client device. Authorization module 332 may also disable a login credential for the particular user if the probability does not exceed the threshold authentication probability.

These techniques may use multiple identification parameters that, in combination, speed access to the client device while ensuring reliable, strong authentication. Biometric sensors that may be utilized with these techniques include a voice recognition sensor, a global positioning system, a shoe tap input sensor, a finger tap input sensor, a hand geometry sensor, a hand grip sensor, a fingerprint sensor, an electrocardiogram sensor, an ear print sensor, a radio frequency identification tag, a proximity sensor, a password entry device, a radio device, a gait sensor, or a keystroke analyzer device. Each authentication device may produce one or more of a passcode, a signature, profile data, authentication data that may be stored on a security device, or biometric information. The authentication factors may also include information that identifies a user as being part of a particular group, and the access granted to the user is in line with general permissions granted to users of that group (e.g., the user is a medic, granting them access to medical information).

Authorization module 332 may intermittently request updates from each of the authentication devices in order to continually verify the identity of the user accessing the client device. In such instances, after sending the authentication confirmation to the client device, authorization module 332 may send, to each of the authentication devices, a request for an updated authentication factor. After receiving the updated authentication factors, authorization module 332 may repeat the above authentication process.

Figure 12:
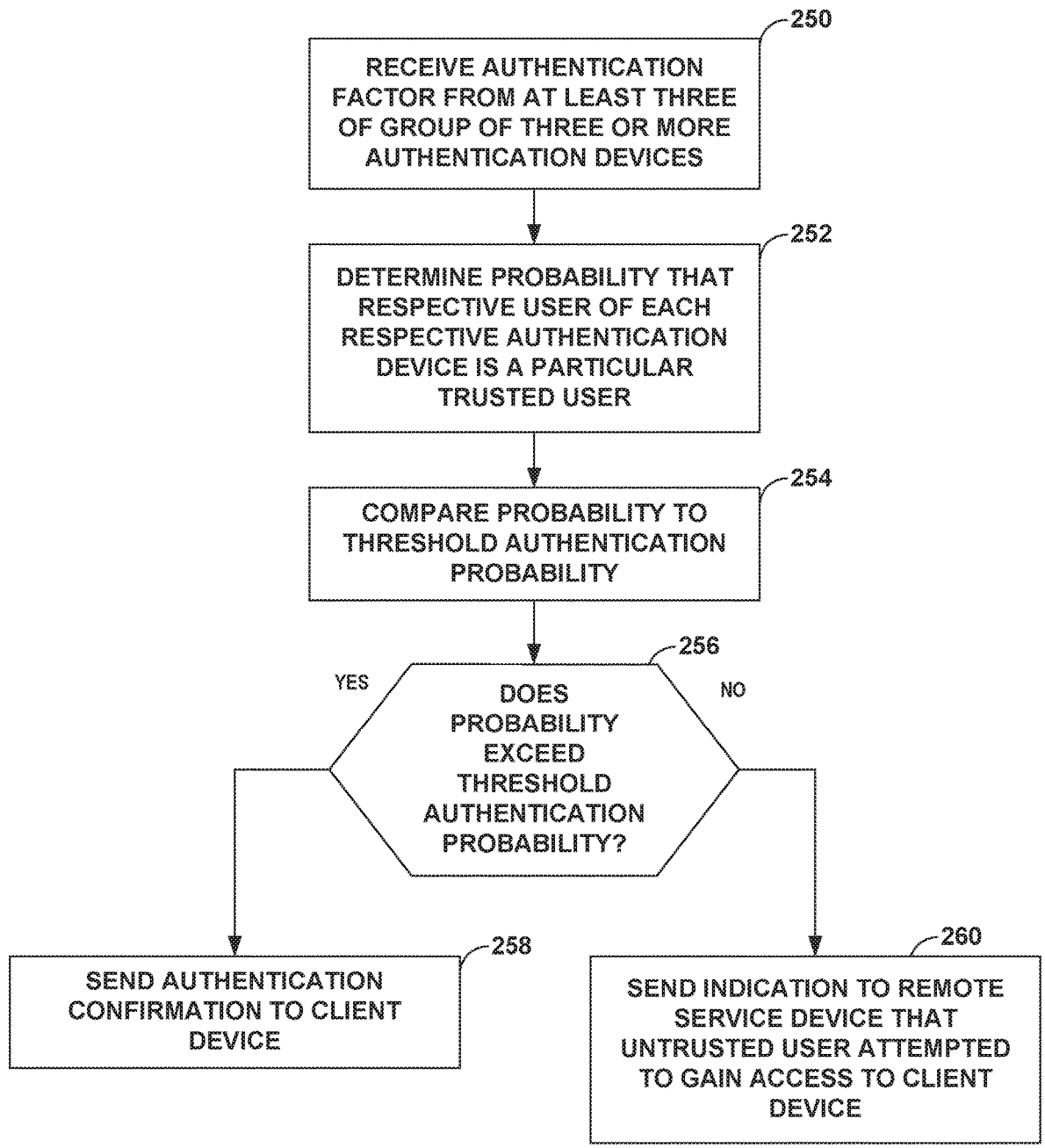
FIG. 12 is a flow diagram illustrating example operations of a server device that implements authentication techniques in accordance with one or more aspects of this disclosure.

FIG. 12 is a flow diagram illustrating example operations of a server device that implements authentication techniques in accordance with one or more aspects of this disclosure. The techniques of FIG. 12 may be performed by one or more processors of a computing device, such as micro-servers 219 illustrated in FIG. 8 or micro-server 219 illustrated in FIG. 11. For purposes of illustration only, the techniques of FIG. 12 are described within the context of micro-server 219 of FIG. 11, although computing devices having configurations different than that of micro-server 219 may perform the techniques of FIG. 12. While the techniques described below with respect to FIG. 12 are described as being performed by processors 314 of micro-server 219, processors 314 may utilize other modules or applications, such as a virtual machine, to perform all or a portion of the techniques described herein, so as to maintain integrity between the secured data packets and the non-secured data packets.

In accordance with the techniques of this disclosure, processors 314 may receive, in a secure domain, an authentication factor from at least three authentication devices of a group of three or more authentication devices (e.g., physiological sensors 218) (250). At least one authentication device in the group of three or more authentication devices is in a non-secure domain. Further, each respective authentication factor comprises a respective identifier of a respective user of the respective authentication device. Processors 314 may determine a probability that the respective user of each respective authentication device is a particular trusted user based on the received authentication factors (252).

Processors 314 may further compare the probability to a threshold authentication probability (254). In this comparison, processors 314 may determine whether the probability exceeds the threshold authentication probability (256). Responsive to determining that the probability exceeds the threshold authentication probability (YES branch of 256), processors 314 may send an authentication confirmation to the client device (e.g., host 4 of FIG. 1) (258), thereby enabling access to one or more applications on the client device. In some instances, in addition to performing the authentication locally, processors 314 may also send the received authentication factors to a remote server for additional confirmation and only enable access to the applications on the client device once the additional confirmation is received from the remote server.

Conversely, responsive to determining that the probability does not exceed the threshold authentication probability (NO branch of 256), in some instances, processors 314 may send an indication to the remote server device that an untrusted user attempted to gain access to the client device (260) to disable a login credential for the particular user. In other instances, responsive to determining that the probability does not exceed the threshold authentication probability, processors 314 may attempt to send the authentication factors and a request to verify the identity of the respective user of the respective authentication device to a remote server and receive one of the identity of the respective user of the respective authentication device or an indication that an untrusted user attempted to gain access to the client device. Processors 314 may also disable a login credential for the particular user if the probability does not exceed the threshold authentication probability.

These techniques may use multiple identification parameters that, in combination, speed access to the client device while ensuring reliable, strong authentication. Biometric sensors that may be utilized with these techniques include a voice recognition sensor, a global positioning system, a shoe tap input sensor, a finger tap input sensor, a hand geometry sensor, a hand grip sensor, a fingerprint sensor, an electrocardiogram sensor, an ear print sensor, a radio frequency identification tag, a proximity sensor, a password entry device, a radio device, a gait sensor, or a keystroke analyzer device. Each authentication device may produce one or more of a passcode, a signature, profile data, authentication data that may be stored on a security device, or biometric information. The authentication factors may also include information that identifies a user as being part of a particular group, and the access granted to the user is in line with general permissions granted to users of that group (e.g., the user is a medic, granting them access to medical information).

Processors 314 may intermittently request updates from each of the authentication devices in order to continually verify the identity of the user accessing the client device. In such instances, after sending the authentication confirmation to the client device, processors 314 may send, to each of the authentication devices, a request for an updated authentication factor. After receiving the updated authentication factors, processors 314 may repeat the above authentication process.

By way of example, and not limitation, such computer-readable storage media can include RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium may include a non-transitory medium. The term "non-transitory" indicates that the storage medium is not embodied in a carrier wave or a propagated signal. In certain examples, a non-transitory storage medium may store data that can, over time, change (e.g., in RAM or cache).

Various examples of the disclosure have been described. Any combination of the described systems, operations, or functions is contemplated. These and other examples are within the scope of the following claims.

What is claimed is:

1. A method comprising:
   receiving, by a server device in a secure domain via a guard device, a respective authentication factor from each of at least three authentication devices in a group of three or more authentication devices, wherein at least one authentication device in the group of three or more authentication devices is in a non-secure domain and authenticatable by the server device in the secure domain, and wherein each respective authentication factor comprises a respective identifier of a respective user of the respective authentication device;
   determining, by the server device, a probability that the respective user of each respective authentication device is a particular trusted user of a client device based on the received respective authentication factors from each of the at least three authentication devices;
   comparing, by the server device, the probability that the respective user of each respective authentication device is the particular trusted user based on the received respective authentication factors to a threshold authentication probability; and
   responsive to determining that the probability exceeds the threshold authentication probability, sending, by the server device to the client device, an authentication confirmation comprising an indication that a particular user using the client device is the particular trusted user.

2. The method of claim 1, further comprising:
   responsive to the probability that the respective user of each respective authentication device is the particular trusted user based on the received respective authentication factors not exceeding the threshold authentication probability, sending, by the server device to a remote server device, an authentication denial comprising an indication that an untrusted user attempted to gain access to the client device.

3. The method of claim 1, further comprising:
   responsive to the probability that the respective user of each respective authentication device is the particular trusted user based on the received respective authentication factors not exceeding the threshold authentication probability, sending, by the server device to a remote server device, the respective authentication factors and a request to verify an identity of the respective user of the respective authentication device; and
   receiving, by the server device from the remote server device, one of the identity of the respective user of the respective authentication device or an indication that an untrusted user attempted to gain access to the client device.

4. The method of claim 1, further comprising:
   responsive to the probability that the respective user of each respective authentication device is the particular trusted user based on the received respective authentication factors not exceeding the threshold authentication probability, sending, by the server device to a remote server, an indication to disable a login credential for the particular user.

5. The method of claim 1, wherein each respective authentication factor comprises one or more of a passcode, a signature, profile data, authentication data stored on a security device, or biometric information.

6. The method of claim 1, wherein a first authentication device of the group of three or more authentication devices comprises one of a voice recognition sensor, a facial recognition camera, a palm vein pattern sensor, a hand geometry sensor, a hand grip sensor, a fingerprint sensor, an electrocardiogram sensor, an ear print sensor, a radio frequency identification tag, a proximity sensor, a password entry device, a radio device, a global positioning system, a shoe tap input sensor, a finger tap input sensor, or a keystroke analyzer device.

7. The method of claim 1, further comprising:
after sending the authentication confirmation to the client device, sending, by the server device to each of the authentication devices, a request for a respective updated authentication factor;
receiving, by the server device, the respective updated authentication factor from each of at least three authentication devices in the group of three or more authentication devices;
determining, by the server device, an updated probability that the respective user of each respective authentication device is the particular trusted user based on the received respective updated authentication factors;
comparing, by the server device, the updated probability that the respective user of each respective authentication device is the particular trusted user based on the received respective updated authentication factors to the threshold authentication probability; and
responsive to the updated probability exceeding the threshold authentication probability, sending, by the server device to the client device, an updated authentication confirmation comprising an updated indication of the particular trusted user.

8. The method of claim 1, wherein the client device is combined with the server device.

9. The method of claim 1, wherein the guard device comprises a one-way guard that enables communication between devices in the non-secure domain and devices in the secure domain, and wherein the guard device is combined with the server device.

10. The method of claim 1, wherein the server device comprises a wearable micro-server device.

11. A server device comprising:
one or more communication units; and
one or more processors configured to:
receive, via a guard device, a respective authentication factor from each of at least three authentication devices in a group of three or more authentication devices, wherein the server device is located in a secure domain, wherein at least one authentication device in the group of three or more authentication devices is in a non-secure domain and authenticatable by the server device in the secure domain, and wherein each respective authentication factor comprises a respective identifier of a respective user of the respective authentication device;
determine a probability that the respective user of each respective authentication device is a particular trusted user of a client device based on the received respective authentication factors from each of the at least three authentication devices;
compare the probability that the respective user of each respective authentication device is the particular trusted user based on the received respective authentication factors to a threshold authentication probability; and
responsive to determining that the probability exceeds the threshold authentication probability, send, to the client device, an authentication confirmation comprising an indication that a particular user using the client device is the particular trusted user.

12. The server device of claim 11, wherein the one or more processors are further configured to:
responsive to the probability that the respective user of each respective authentication device is the particular trusted user based on the received respective authentication factors not exceeding the threshold authentication probability, send, to a remote server device, an authentication denial comprising an indication that an untrusted user attempted to gain access to the client device.

13. The server device of claim 11, wherein the one or more processors are further configured to:
responsive to the probability that the respective user of each respective authentication device is the particular trusted user based on the received respective authentication factors not exceeding the threshold authentication probability, send, to a remote server device, the respective authentication factors and a request to verify an identity of the respective user of the respective authentication device; and
receive, from the remote server device, one of the identity of the respective user of the respective authentication device or an indication that an untrusted user attempted to gain access to the client device.

14. The server device of claim 11, wherein the one or more processors are further configured to:
responsive to the probability that the respective user of each respective authentication device is the particular trusted user based on the received respective authentication factors not exceeding the threshold authentication probability, send, to a remote server, an indication to disable a login credential for the particular user.

15. The server device of claim 11, wherein each respective authentication factor comprises one or more of a passcode, a signature, profile data, authentication data stored on a security device, or biometric information.

16. The server device of claim 11, wherein a first authentication device of the group of three or more authentication devices comprises one of a voice recognition sensor, a global positioning system, a shoe tap input sensor, a finger tap input sensor, a hand geometry sensor, a hand grip sensor, a fingerprint sensor, an electrocardiogram sensor, an ear print sensor, a radio frequency identification tag, a proximity sensor, a password entry device, a radio device, or a keystroke analyzer device.

17. The server device of claim 11, wherein the one or more processors are further configured to:
after sending the authentication confirmation to the client device, send, to each of the authentication devices, a request for a respective updated authentication factor;
receive the respective updated authentication factor from each of at least three authentication devices in the group of three or more authentication devices;

determine an updated probability that the respective user of each respective authentication device is the particular trusted user based on the received respective updated authentication factors;

compare the updated probability that the respective user of each respective authentication device is the particular trusted user based on the received respective updated authentication factors to the threshold authentication probability; and responsive to the updated probability exceeding the threshold authentication probability, send, to the client device, an updated authentication confirmation comprising an updated indication of the particular trusted user.

18. The server device of claim 11, wherein the server device comprises a wearable micro-server device.

19. A non-transitory computer readable storage medium storing instructions that, when executed by one or more processors of a server device cause the one or more processors to:

receive, via a guard device, a respective authentication factor from each of at least three authentication devices in a group of three or more authentication devices, wherein the server device is located in a secure domain, wherein at least one authentication device in the group of three or more authentication devices is in a non-secure domain and authenticatable by the server device in the secure domain, and wherein each respective authentication factor comprises a respective identifier of a respective user of the respective authentication device;

determine a probability that the respective user of each respective authentication device is a particular trusted user of a client device based on the received respective authentication factors from each of the at least three authentication devices;

compare the probability that the respective user of each respective authentication device is the particular trusted user based on the received respective authentication factors to a threshold authentication probability; and responsive to determining that the probability exceeds the threshold authentication probability, send, to the client device, an authentication confirmation comprising an indication that a particular user using the client device is the particular trusted user.

20. The non-transitory computer readable storage medium of claim 19, wherein the instructions further cause the one or more processors to:

after sending the authentication confirmation to the client device, send, to each of the authentication devices, a request for a respective updated authentication factor;

receive the respective updated authentication factor from each of at least three authentication devices in the group of three or more authentication devices;

determine an updated probability that the respective user of each respective authentication device is the particular trusted user based on the received respective updated authentication factors;

compare the updated probability that the respective user of each respective authentication device is the particular trusted user based on the received respective updated authentication factors to the threshold authentication probability; and responsive to the updated probability exceeding the threshold authentication probability, send, to the client device, an updated authentication confirmation comprising an updated indication of the particular trusted user.

\* \* \* \* \*